United States Patent
Patton et al.

(10) Patent No.: US 12,173,032 B2
(45) Date of Patent: *Dec. 24, 2024

(54) RECOMBINANT ROTAVIRUS EXPRESSION SYSTEM AND RECOMBINANT ROTAVIRUSES

(71) Applicant: The Trustees of Indiana University, Bloomington, IN (US)

(72) Inventors: John Thomas Patton, Bloomington, IN (US); Asha Ann Philip, Bloomington, IN (US)

(73) Assignee: The Trustees of Indiana University, Bloomington, IN (US)

(*) Notice: Subject to any disclaimer, the term of this patent is extended or adjusted under 35 U.S.C. 154(b) by 590 days.

This patent is subject to a terminal disclaimer.

(21) Appl. No.: 17/259,844

(22) PCT Filed: Jul. 12, 2019

(86) PCT No.: PCT/US2019/041677
§ 371 (c)(1),
(2) Date: Jan. 12, 2021

(87) PCT Pub. No.: WO2020/014654
PCT Pub. Date: Jan. 16, 2020

(65) Prior Publication Data
US 2021/0269488 A1    Sep. 2, 2021

Related U.S. Application Data

(60) Provisional application No. 62/697,869, filed on Jul. 13, 2018.

(51) Int. Cl.
| | | |
|---|---|---|
| C07K 14/005 | (2006.01) | |
| A61K 39/15 | (2006.01) | |
| C12N 7/00 | (2006.01) | |
| A61K 39/00 | (2006.01) | |

(52) U.S. Cl.
CPC .......... *C07K 14/005* (2013.01); *A61K 39/15* (2013.01); *C12N 7/00* (2013.01); *A61K 2039/5254* (2013.01); *C12N 2720/12321* (2013.01); *C12N 2720/12322* (2013.01); *C12N 2720/12334* (2013.01); *C12N 2720/12351* (2013.01)

(58) Field of Classification Search
None
See application file for complete search history.

(56) References Cited

U.S. PATENT DOCUMENTS

| | | |
|---|---|---|
| 5,952,474 A | 9/1999 | Kayman |
| 7,396,664 B2 | 7/2008 | Daly |
| 2010/0322962 A1 | 12/2010 | Jiang |
| 2013/0280293 A1 | 10/2013 | Kuppuswamy |

FOREIGN PATENT DOCUMENTS

| | | | |
|---|---|---|---|
| JP | 20190050796 | * | 4/2019 |
| WO | 2008009727 A1 | | 1/2008 |
| WO | 2010042490 A1 | | 4/2010 |
| WO | 2017/062246 | | 4/2017 |
| WO | 2018/062199 | | 4/2018 |
| WO | 2021216575 A1 | | 10/2021 |
| WO | 2023069950 A1 | | 4/2023 |

OTHER PUBLICATIONS

Gratia et al. PLoSone vol. 11, No. 1, pp. 1-24 (Year: 2016).*
Bishop, J of Gastroenterology and Hepatology 24 Sup3, S81-S85 (Year: 2005).*
Gratia et al., PLOS One 11(1) e0145998 (Year: 2016).*
Komoto et al., Journal of Virology vol. 92, No. 13, pp. 1-15 (Year: 2019).*
Eaton et al., Journal of Virology vol. 91 Issue 11 e02416-16 (Year: 2017).*
Komoto et al. JP2019050796 from IDS, translation from WIPO (Year: 2019).*
Shane D. Trask, et al., "Dual selection mechanisms drive efficient single-gene reverse genetics for rotavirus", PNAS, Oct. 26, 2010, vol. 107, No. 43; pp. 18652-18657.
Cecile Troupin, et al., "Rearranged Genomic RNA Segments Offer a New Approach to the Reverse Genetics of Rotaviruses", Journal of Virology, Jul. 2010, vol. 84, No. 13; p. 6711-6719.
Sharia M. Ahmed, et al., "Global prevalence of norovirus in cases of gastroenteritis a systematic review and meta-analysis", www.thelancet.com/infection, vol. 14, published online Jun. 27, 2014; 6 pages.
Benjamin A. Lopman, et al., "The Vast and Varied Global Burden of Norovirus: Prospects for Prevention and Control", PLOS Medicine, Apr. 26, 2016; 12 pages.
Daniel C. Payne, PH.D., et al., "Norovirus and Medically Attended Gastroenteritis in U.S. Children", The New England Journal of Medicine, NEJM.org, Mar. 21, 2013; 10 pages.
Jelle Matthijnssens, et al., "Group A rotavirus universal mass vaccination: how and to what extent will selective pressure influence prevalence of rotavirus genotypes?", Expert Reviews Ltd.; 2012; 17 pages.
Daniel E. Velasquez, et al., "Strain diversity plays no major role in the varying efficacy of rotavirus vaccines: An overview", Infections, Genetics and Evolutions 28 (2014); pp. 561-571.

(Continued)

*Primary Examiner* — Shanon A. Foley
*Assistant Examiner* — Myron G Hill
(74) *Attorney, Agent, or Firm* — Quarles & Brady, LLP

(57) ABSTRACT

Embodiments herein report compositions, methods, uses and manufacturing procedures for rotavirus constructs and immunogenic compositions thereof. Some embodiments concern compositions that include, but are not limited to, chimeric rotaviruses of use in immunogenic compositions against rotavirus infection as well as against other pathogenic virus infection in a subject. In certain embodiments, constructs of use herein can be generated and used where a rotavirus expression system further includes one or more nucleic acid molecules encoding one or more polypeptides of another pathogen (e.g. another enteric or mucosal pathogen).

17 Claims, 14 Drawing Sheets

Specification includes a Sequence Listing.

(56) References Cited

OTHER PUBLICATIONS

Jacqueline E. Tate, et al., "Remaining issues and challenges for rotavirus vaccine in preventing global childhood diarrheal morbidity and mortality", Expert Reviews Ltd., 2012; 21 pages.
Soares-Weiser K, et al., "Vaccines for preventing rotavirus diarrhoea: vaccines in use (Review)", Cochrane Library, Cochrane Database of Systematic Reviews 2019, issue 10; 268 pages.
Krisztian Banyai, et al., "Systematic review of regional and temporal trends in global rotavirus strain diversity in the pre rotavirus vaccine era: Insights for understanding the impact of rotavirus vaccination programs", SciVerse Science Direct, Vaccine 30S (2012), A122-A130; 9 pages.
Laura M. Lamberti, PH.D., et al., "Systematic Review of the Effect of Rotavirus Vaccination on Diarrhea Outcomes Among Children Younger Than 5 Years", The Pediatric Infectious Disease Journal, vol. 35, No. 9, Sep. 2016; 7 pages.
Jacqueline E. Tate, et al., "Global, Regional, and National Estimates of Rotovirus Mortality in Children <5 Years of Age, 2000-2013", Infectious Diseases Society of America, HIV Medicine Association, 2016:62; 10 pages.
Jelle Matthijnssens, et al., "Uniformity of rotavirus strain nomenclature proposed by the Rotavirus Classification Working Group (RCWG)", Arch Virol, 2011, 156:1397-1413; 17 pages.
Jelle Matthijnssens, et al., "Genotype constellation and evolution of group A rotaviruses infecting humans", SciVerse ScienceDirect, www.sciencedirect.com, 2012; 8 pages.
Vytautas Usonis, et al., "The unpredictable diversity of co-circulating rotavirus types in Europe and the possible impact pf universal mass vaccination programmes on rotavirus genotype incidence", Vaccine 30, 2012, SciVerse ScienceDirect; 10 pages.
Ulrich Desselberger, "Rotaviruses", Virus Research, 190, 2014; pp. 75-96.
Kristen M. Ogden, et al., "Structural Basis for 2'-5'-Oligoadenylate Binding and Enzyme Activity of a Viral RNase L Antagonist", Journals.ASM.org, Journal of Virology, Jul. 2015, vol. 89, No. 13; 13 pages.
Jelle Matthijnssens, et al., "VP6-sequence-based cutoff values as a criterion for rotavirus species demarcation", Arch Virol, 2012, 157: 1177-1182.
Hao Fang, et al., "Norovirus P Particle Efficiently Elicits Innate, Humoral and Cellular Immunity", PLOS, One, Apr. 2013, vol. 8, issue 4; 10 pages.
Marco Morelli, et al., "Silencing the alarms: Innate immune antagonism by rotavirus NSP1 and VP3", Virology 479-480, 2018; 10 pages.
Sarah M. McDonald, et al., "Evolutionary Dynamics of Human Rotaviruses: Balancing Reassortment with Preferred Genome Constellations", PLOS Pathogens, Oct. 2009, vol. 5, issue 10; 14 pages.
Rong Zhang, et al., "Homologous 2',5'-phosphodiesterases from disparate RNA viruses antagonize antiviral innate Immunity", PNAS, Aug. 6, 2013, vol. 110, No. 32; 6 pages.
Daichi Kamiyama, et al., "Versatile protein tagging in cells with split fluorescent protein", Nature Communications, Mar. 18, 2016; 9 pages.
Erica M. Heiman, et al., "Group A Human Rotavirus Genomics: Evidence that Gene Constellations Are Influenced by Viral Protein Interactions", Journal of Virology, Nov. 2008; 11 pages.
Aleksander A. Demidenko, et al., "Engineering recombinant reoviruses with tandem repeats and a tetravirus 2A-like element for exogenous polypeptide expression", PNAS, Apr. 29, 2013; 10 pages.
Jin Hee-Kim, et al., "High Cleavage Efficiency of a 2A Peptide Derived from Porcine Teschovirus-1 in Human Cell ines, Zebrafish and Mice", PLOS One, Apr. 2011, vol. 6, issue 4; 8 pages.
Hilda Montero, et al., "Rotavirus Nonstructural Protein NSP3 is Not Required for Viral Protein Synthesis", Journal of Virology, Sep. 2006 vol. 8, No. 18; 8 pages.
Caroline M. Groft, et al., "Recognition of eIF4G by Rotavirus NSP3 Reveals a Basis for mRNA Circularization", Molecular Cell, vol. 9, 1273-1283, Jun. 2002; 11 pages.
Rahul C. Deo, et al., "Recognition of the Rotavirus mRNA 3' Consensus by an Asymmetric NSP3 Homodimer", Cell, vol. 108, 71-81, Jan. 11, 2002; 11 pages.
Ningguo Feng, et al., "Permissive Replication of Homologous Murine Rotavirus in the Mouse Intestine Is Primarily Regulated by VP4 and NSP1", Journals.ASM.org, Journal of Virology, Aug. 2013, vol. 87, No. 15; 10 pages.
Michelle Arnold, et al., "Culturing, Storage, and Quantification of Rotaviruses", NIH Public Access, Curr Protoc Microbiol, Nov. 2009, CHAPTER: Unit 15C.3; 29 pages.
Satoshi Komoto, et al., "A plasmid-based reverse genetics system for mammalian orthoreoviruses driven by a plasmid-encoded T7 RNA polymerase", Journal of Virological Methods 196, 2014; 36-39 pages.
Eiko Matsuo, et al., "Bluetongue Virus VP6 Acts Early in the Replication Cycle and Can Form the Basis of Chimeric Virus Formation", Journal of Virology, Sep. 2009, vol. 83, No. 17; 7 pages.
Tomas Lopez, et al., "Heat Shock enhances the susceptibility of BHK cells to rotavirus infection through the facilitation of entry and post-entry virus replication steps", Science Direct, Virus Research 121, 2006; 10 pages.
Mark Boyce, et al., "Development of Reverse Genetics Systems for Bluetongue Virus: Recovery of Infectious Virus from Synthetic RNA Transcripts", American Society for Microbiology, Journal of Virology, Sep. 2008, vol. 82, No. 17; 10 pages.
Aitor Navarro, et al., "Generation of Genetically Stable Recombinant Rotaviruses Containing Novel Genome Rearrangements and Heterologous Sequences by Reverse Genetics", Journals.ASM.org, Journal of Virology, Jun. 2013, vol. 87, No. 11; 10 pages.
Karl W. Boehme, et al., "Reverse genetics for mammalian reovirus", Methods 55, Science Direct, 2011; 5 pages.
Takeshi Kobayashi, et al., "An improved reverse genetics system for mammalian orthoreoviruses", Virology, 2010, 398, Science Direct; 7 pages.
Michael R. Roner, et al., "Reovirus RNA is Infectious", Virology 179, 1990; 8 pages.
Shane D. Trask, et al., "Structural insights into the coupling of virion assembly and rotavirus replication", Nature Reviews Microbiology, vol. 10, Mar. 2012; 13 pages.
Michelle M. Arnold, et al., "Rotavirus variant replicates efficiently although encoding an aberrant NSP3 that fails to induce nuclear localization of poly(A)-binding protein", Journal of General Virology, 2012, 93; 12 pages.
Akiko Kumagai, et al., "A Bilirubin-Inducible Fluorescent Protein from Eel Muscle", Cell 153, 1601-1611, Jun. 20, 2013; 10 pages.
Jeffrey O. Langland, et al., "Products of the Porcine Group C Rotavirus NSP3 Gene Bind Specifically to Double-Stranded RNA and Inhibit Activation of the Interferon-Induced Protein Kinase PKR", Journal of Virology, Jun. 1994, vol. 68, No. 6; 9 pages.
James E. Richards, et al., "Experimental Pathways towards Developing a Rotavirus Reverse Genetics System: Synthetic Full Length Rotavirus ssRNAs Are Neither Infectious nor Translated in Permissive Cells", PLOS One, Sep. 2013, vol. 8, issue 9; 16 pages.
Vivienne L.A. James, et al., "Molecular characterization of human group C rotavirus genes 6, 7 and 9", Journal of General Virology, 1990, 80; 7 pages.
Michelle L.L. Donnelly, et al., "The 'cleavage' activities of foot-and-mouth disease virus 2A site-directed mutants and naturally occurring '2A-like' sequences", Journal of General Virology, 2001, 82; 15 pages.
Garry A. Luke, et al., "The protein coexpression problem in biotechnology and biomedicine: virus 2A and 2A-like sequences provide a solution", Future Medicine Ltd, 2013; 23 pages.
Garry A. Luke, et al., "Occurrence, function and evolutionary origins of '2A-like' sequences in virus genomes", Journal of General Virology (2008), 89, pp. 1036-1042.
Jakobus M. Pretorius, et al., "Establishment of an entirely plasmid-based reverse genetics system for Bluetongue virus", Virology 486 (2015) 71-77.
Reimar Johne, et al., "Generation of an Avian-Mammalian Rotavirus Reassortant by Using a Helper Virus-Dependent Reverse Genet-

(56) References Cited

OTHER PUBLICATIONS ics System", American Society for Microbiology Journal of Virology, Feb. 2016, vol. 90, No. 3; 5 pages.
International Search Report issued by the International Searching Authority, dated Oct. 11, 2019, for International Patent Application No. PCT/US2019/41677; 4 pages.
Gratia, M. et al. "Challenging the Roles of NSP3 and Untranslated Regions in Rotavirus mRNA Translation. PLoSOne." Jan. 4, 2016, vol. 11, No. 1, pp. 1-24.
James, Vla, et al. "Molecular characterization of human group C rotavirus genes 6, 7 and 9", Journal of General Virology. Dec. 1999, vol. 80, No. 12, pp. 3181-3187.
Kanai, Y et al. "Entirely plasmid-based reverse genetics system for rotaviruses." Proceedings of the National Academy of Sciences of the U.S.A., Feb. 28, 2017, Epub Jan. 30, 2017, vol. 114, No. 9, pp. 2349-2354.
Komoto, et al. "Generation of Recombinant Rotaviruses Expressing Fluorescent Proteins by Using an Optimized Reverse Genetics System", Journal of Virology, Apr. 18, 2018, vol. 92, No. 13, pp. 1-15.
Written Opinion of the International Searching Authority, dated Oct. 11, 2019, for International Patent Application No. PCT/US2019/41677; 8 pages.
Takeshi Kobayashi, et al., "A Plasmid-Based Reverse Genetics System for Animal Double-Stranded RNA Viruses", Cell Host & Microbe Resource, Apr. 2007, 147-157.
Satoshi Komoto, et al., "Reverse genetics system for introduction of site-specific mutations into the double-stranded RNA genome of infectious rotavirus", PNAS, Mar. 21, 2006, vol. 103, No. 12; 6 pages.
A. Navarro, et al., "Rotavirus Replication and Reverse Genetics", Chapter 2.3 Elsevier Science & Technology, copyright 2016; 24 pages.
Ulrich Desselberger, "Rotaviruses", ScienceDirect Virus Research 190 (2014), 75-96.
Michelle L. L. Donnelly, et al., "The 'cleavage' activities of foot-and-mouth disease virus 2A site-directed mutants and naturally occurring '2A-like' sequences", Journal of General Virology (2001), 82, 1027-1041.
Aleksander A. Demidenko, et al., "Engineering recombinant reoviruses with tandem repeats and a tetravirus 2A-like element for exogenous polypeptide expression", PNAS, published online Apr. 29, 2013; 10 pages.
Rahul C. Deo, et al., "Recognition of the Rotavirus mRNA 3' Consensus by an Asymmetric NSP3 Homodimer", Cell Press, vol. 108, 71-81, Jan. 11, 2002; 11 pages.
Kari Debbink, et al., "The State of Norovirus Vaccines", Vaccines Invited Article, 1746, CID 2014:58, Jun. 2015; 7 pages.
Nicolas W. Cortes-Penfield, MD, et al., "Prospects and Challenges in the Development of a Norovirus Vaccine", Clinical Therapeutics, vol. 39, No. 8, 2017; 13 pages.
Gael Belliot, et al., "In Vitro Proteolytic Processing of the MD145 Norovirus ORF1 Nonstructural Polyprotein Yields Stable Precursors and Products Similar to Those Detected in Calicivirus-Infected Cells", Journal of Virology, Oct. 2003, vol. 77, No. 20; p. 10957-10974.
F. Baehner, et al., "Vaccines against norovirus: state of the art trials in children and adults", Clinical Microbiology and Infection 22 (2016), S136-S139.
Marli S.P. Azevedo, et al., "An Oral versus Intranasal Prime/Boost Regimen Using Attenuated Human Rotavirus or VP2 and VP6 Virus-Like Particles with Immunostimulating Complexes Influences Protection and Antibody-Secreting Cell Responses to Rotavirus in a Neonatal Gnotobiotic Pig Model", Clinical and Vaccine Immunology, Mar. 2010, p. 420-428.
Michelle M. Arnold, et al., "Rotavirus variant replicates efficiently although encoding an aberrant NSP3 that fails to induce nuclear localization of poly(A)-binding protein", Journal of General Virology (2012), 93, 1483-1494.

Robert L. Atmar, et al., "Rapid Responses to 2 Virus-Like Particle Norovirus Vaccine Candidate Formulations in Healthy Adults: A Randomized Controlled Trial", The Journal of Infectious Diseases Major Article, Sep. 2015; 9 pages.
Lijuan Yuan, et al., "Systemic and Intestinal Antibody-Secreting Cell Responses and Correlates of Protective Immunity to Human Rotavirus in a Gnotobiotic Pig Model of Disease", Journal of Virology, May 1996, p. 3075-3083.
Sharia M. Ahmed, et al., "Global prevalence of norvirus in cases of gastroenteritis: a systematic review and meta-analysis", www.thelancet.com/infection, vol. 14, Aug. 2014; 6 pages.
Lijuan Yuan, et al., "Induction of mucosal immune responses and protection against enteric viruses: rotavirus infection of gnotobiotic pigs as a model", Veterinary Immunology and Immunopathology 87(2002); 14 pages.
Johannes F. Wentzel, et al., "Consensus sequence determination and elucidation of the evolutionary history of a rotavirus Wa variant reveal a close relationship to various Wa variants derived from the original Wa strain", Infection, Genetics and Evolution 20 (2013) 276-283.
Vivek Verma, et al., "Norovirus (NoV) specific protective immune responses induced by recombinant P dimer vaccine are enhanced by the mucosal adjuvant FlaB", Journal of Translational Medicine, 2016, 14:135; 12 pages.
L.A. Ward, et al., "Pathogenesis of an attenuated and a virulent strain of group A human rotavirus in neonatal gnotobiotic pigs", Journal of General Virology (1996), 77, 1431-1441; 11 pages.
Shane D. Trask, et al., "Dual selection mechanisms drive efficient single-gene reverse genetics for rotavirus", PNAS, Oct. 26, 2010, vol. 107, No. 43; 6 pages.
Jacqueline E. Tate, et al., "Global, Regional, and National Estimates of Rotavirus Mortality in Children <5 Years of Age, 2000-2013", IDSA, Clinical Infectious Diseases Supplemental Article, 2016:62 (Suppl 2); 10 pages.
Ming Tan, et al., "Terminal modifications of norovirus P domain resulted in a new type of subviral particles, the small P particles", Virology 410 (2011); pp. 345-352.
Soares-Weiser K, et al., "Vaccines for preventing rotavirus diarrhoea: vaccines in use (Review)", Cochrane Library, 2019; 268 pages.
W. Su, et al., "Production, characterization and immunogenicity of P particles derived from norovirus GII.4 genotype 2004 variant", Acta virologica 59: 33-39, 2015; 7 pages.
Lynn S. Silvestri, et al., "Rotavirus Replication: Plus-Sense Templates for Double-Stranded RNA Synthesis Are Made in Viroplasms", Journal of Virology, Jul. 2004, vol. 78, No. 14; 12 pages.
Daniel C. Payne, Ph.D., et al., "Norovirus and Medically Attended Gastroenteritis in U.S. Children", The New England Journal of Medicine 368;12, Mar. 21, 2013; 10 pages.
John T. Patton, et al., "Effect of Intragenic Rearrangement and Changes in the 3' Consensus Sequence on NSP1 Expression and Rotavirus Replication", Journal of Virology, Mar. 2001, vol. 75, No. 5; p. 2076-2086.
Jelle Matthijnssens, et al., "Uniformity of rotavirus strain nomenclature proposed by the Rotavirus Classification Working Group (RCWG)", Arch Virol (2011) 156: 1397-1413.
Aitor Navarro, et al., "Generation of Genetically Stable Recombinant Rotaviruses Containing Novel Genome Rearrangements and Heterologous Sequences by Reverse Genetics", Journal of Virology, Jun. 2013, vol. 87, No. 11; 10 pages.
Marco Morelli, et al., "Silencing the alarms: Innate immune antagonism by rotavirus NSP1 and VP3", Virology 479-480 (2015); pp. 75-84.
Hilda Montero, et al., "Rotavirus Nonstructural Protein NSP3 Is Not Required for Viral Protein Synthesis", Journal of Virology, Sep. 2006; pp. 9031-9038.
Jelle Matthijnssens, et al., "Genotype constellation and evolution of group A rotaviruses infecting humans", SciVerse ScienceDirect, 2012; 8 pages.
Lisa C. Lindesmith, et al., "Immunogenetic Mechanisms Driving Norovirus GII.4 Antigenic Variation", PLOS Pathogens, www.plospathogens.org, May 2012, vol. 8, issue 5; 18 pages.

(56) References Cited

OTHER PUBLICATIONS

Garry A. Luke and Martin D. Ryan, "Using the 2A Protein Coexpression System: Multicistronic 2A Vectors Expressing Gene(s) of Interest and Reporter Proteins", Chapter 3 of Springer Nature 2018; 18 pages.
Akiko Kumagai, et al., "A Bilirubin-Inducible Fluorescent Protein from Eel Muscle", Cell 153, Jun. 20, 2013; pp. 1602-1611.
Jeffrey O. Langland, et al., "Products of the Porcine Group C Rotavirus NSP3 Gene Bind Specifically to Double-Stranded RNA and Inhibit Activation of the Interferon-Induced Protein Kinase PKR", Journal of Virology, Jun. 1994, vol. 68, No. 6; pp. 3821-3829.
Laura M. Lamberti, PhD, et al., "A Systematic Review of the Effect of Rotavirus Vaccination on Diarrhea Outcomes Among Children Younger Than 5 Years", The Pediatric Infectious Disease Journal, vol. 35, No. 9, Sep. 2016; 7 pages.
Satoshi Komoto, et al., "Reverse Genetics System Demonstrates that Rotavirus Nonstructural Protein NSP6 Is Not Essential for Viral Replication in Cell Culture", Journal of Virology, American Society for Microbiology, Nov. 2017, vol. 91, issue 21; 10 pages.
Jacob Kocher, et al., "Intranasal P Particle Vaccine Provided Partial Cross-Variant Protection against Human GII.4 Norovirus Diarrhea in Gnotobiotic Pigs", Journal of Virology, Sep. 2014, vol. 88, No. 17; 16 pages.
Jin Hee Kim, et al., "High Cleavage Efficiency of a 2A Peptide Derived from Porcine Teschovirus-1 in Human Cell Lines, Zebrafish and Mice", PLOS One, www.plosone.org, Apr. 2011, vol. 6, issue 4; 8 pages.
Yuta Kanai, et al., "Entirely plasmid-based reverse genetics system for rotaviruses", PNAS, Feb. 28, 2017, vol. 114, No. 9; 6 pages.
Stephanie M. Karst, et al., "Advances in Norovirus Biology", Cell Host & Microbe 15, Jun. 11, 2014; 13 pages.
Vivienne L.A. James, et al., "Molecular characterization of human group C rotavirus genes 6, 7 and 9", Journal of General Virology (1999), 80, pp. 3181-3187.
Heath E. Eaton, et al., "African Swine Fever Virus NP868R Capping Enzyme Promotes Reovirus Rescue during Reverse Genetics by Promoting Reovirus Protein Expression, Virion Assembly, and RNA Incorporation into Infectious Virions", Journal of Virology, Jun. 2017, vol. 91, issue 11; 21 pages.
Michele E. Hardy, "Norovirus protein structure and function", FEMS Microbiology Letters 253 (2015); pp. 1-8.
Caroline M. Groft, et al., "Recognition of eIF4G by Rotavirus NSP3 Reveals a Basis for mRNA Circularization", Molecular Cell, vol. 9, Jun. 2002; pp. 1273-1283.
Hao Fang, et al., "Norovirus P Particle Efficiently Elicits Innate, Humoral and Cellular Immunity", PLOS One, www.plosone.org, Apr. 2013, vol. 8, issue 4; 10 pages.
Barro, M. & Patton, J.T., "Rotavirus NSP1 inhibits expression of type I interferon by antagonizing the function of interferon regulatory factors IRF3, IRF5, and IRF7." J Virol. May 2007; 81(9):4473-4481.
Blazevic, V., et al., "Norovirus VLPs and rotavirus VP6 protein as combined vaccine for childhood gastroenteritis." Vaccine. Oct. 19, 2011; 29(45):8126-33.
Clapp, L.L. & Patton, J.T., "Rotavirus morphogenesis: domains in the major inner capsid protein 710 essential for binding to single-shelled particles and for trimerization." Virology, 1991; 180(2):697-708.
Desselberger, U. "Genome rearrangements of rotaviruses." Adv Virus Res. 1996;46:69-95.
Deval, J., et al., "Structure(s), function(s), and inhibition of the RNA-dependent RNA polymerase of noroviruses." Virus Res. Apr. 15, 2017; 234:21-33.
Falkenhagen, A., et al., "Generation of simian rotavirus reassortants with diverse VP4 genes using reverse genetics." Journal of General Virology 2019; 100:1595-1604.
Gault, E., et al., "A human rotavirus with rearranged genes 7 and 11 encodes a modified NSP3 protein and suggests an additional mechanism for gene rearrangement." J Virol. 2001 Au; 75(16):7305-14.
Gorziglia, M., et al., "Biochemical evidence for the oligomeric (possibly trimeric) structure of the major inner capsid polypeptide (45K) of rotaviruses." J Gen Virol. Sep. 1985; 66(Pt 9): 1889-900/.
Gratia, M., et al., "Rotavirus NSP3 Is a Translational Surrogate of the Poly(A) Binding Protein-687 Poly(A) Complex." J Virol 2015; 89(17):8773-82.
Harb, M., et al., "Nuclear localization of cytoplasmic Poly(A)-binding protein upon rotavirus infection involves the interaction of NSP3 with eIF4G adn RoxaN." J Virol. Nov. 2008; 82(22):11283-11293.
International Search Report and Written Opinion, for corresponding PCT Application No. PCT/US2022/078305, Issued Feb. 22, 2023, 20 pages.
Kanai, Y., et al., "Development of stable rotavirus reporter expression systems." J Virol. Feb. 5, 2019; 93(4):e01774-18.
Kawagishi, T., et al., Reverse genetics system for a human group A rotavirus. J Virol 2020; 94(2):e00963-19.
Kojima, K., et al., "Sequence analysis of normal and rearranged NSP5 genes from human rotavirus strains isolated in nature: implications for hte occurrence of the rearrangement at the step of plus strand synthesis." Virology. Oct. 15, 1996; 224(2):446-52.
Komoto, S., et al. "Generation of infectious recombinant human rotaviruses from just 11 cloned cDNAs encoding the rotavirus genome." J Virol 2019; 93(8):e02207-18.
Kroneman, A., et al., "Proposal for a unified norovirus nomenclature and genotyping." Arch Virol. Oct. 2013; 158 (10):2059-68.
Lappalainen, S., et al., "Protection against live rotavirus challenge in mice induced by parenteral and mucosal delivery of VP6 subunit rotavirus vaccine." Arch Virol. Aug. 2015; 160(8):2075-8.
Malm, M., et al., Rotavirus recombinant VP6 nanotubes act as an immunomodulator and delivery vehicle for norovirus virus-like particles. Journal of immunology research 2016; 2016:9171632.
Mattison, C.P., et al., "Progress on norovirus vaccine research:public health considerations and future directions." Expert Rev Vaccines Sep. 2018; 17(9):773-784.
McDonald, S.M. & Patton, J.T., "Assortment and packaging of the segmented rotavirus genome." Trends Microbiol. Mar. 2011; 19(3):136-44.
McIntyre, M., et al., "Biophysical characterization of rotavirus particles containing rearranged genomes." J Gen Virol Nov. 1987; 68 ( Pt 11):2961-6.
Netzler, N.E., et al., "Norovirus antivirals: where are we now?" Med Res Rev. May 2019; 39(3):860-886.
Papa, G., et al., "Recombinant rotaviruses rescued by reverse genetics reveal the role of NSP5 hyperphosphorylation in the assembly of viral factories." J. Virol. Dec. 12, 2019; 94(1):e01110-19.
Pesavento, J.B., et al., "Rotavirus proteins: structure and assembly." Curr Top Microbiol Immunol. 2006;309:189-219.
Philip, A.A., & Patton, J.T. "Expression of separate heterologous proteins from the rotavirus NSP3 genome segment using a translational 2A stop-restart element." J Virol, Sep. 2020; 94(18):e00959-20.
Philip, A.A., & Patton, J.T. "Rotavirus as an expression platform of domains of the SARS-CoV-2 spike protein." Vaccines 2021; 9(5):449.
Philip, A.A., et al. "Generation of recombinant rotavirus expressing NSP3-UnaG fusion protein by a simplified reverse genetics system." Journal of Virology, Nov. 26, 2019; 93(24).
Philip, A.A., et al., "Collection of recombinant rotaviruses expressing fluorescent reporter proteins." Microbiol Resour Announc, Jul. 3, 2019; 8(27): e00523-19.
Philip, A.A., et al., "Simplified reverse genetics method to recover recombinant rotaviruses expressing reporter proteins." J Vis Exp Immunology and Infection, Apr. 17, 2020; 158:e61039.
Piron, M., et al., "Identification of the RNA-binding, dimerization, and eIF4GI-binding domains of rotavirus nonstructural protein NSP3." J Virol. Jul. 1999; 73(7):5411-21.
Pogan, R., et al., "Norovirus assembly and stability." Curr Opin Virol. Aug. 2018; 31:59-65.
Shen, S., et al., "Rearrangement of the VP6 gene of a group A rotavirus in combination with a point mutation affecting trimer stability." J Virol 1994; 68:1682-1688.

(56) References Cited

OTHER PUBLICATIONS

Tan, M. & Jiang, X. "Vaccine against norovirus." Hum Vaccin Immunother. 2014; 10(6):1449-56.
Tresset, G., et al., "Norovirus capsid proteins self-assemble through biphasic kinetics via long-lived stave-like intermediates." J Am Chem Soc. Oct. 16, 2013; 135(41):15373-81.
Tubiana, T., et al. "Dynamics and asymmetry in the dimer of hte norovirus major capsid protein." PLoS One 2017; 12: e0182056-e0182056.

* cited by examiner

| | |
|---|---|
| 1 | SA11-4F |
| 2 | rSA11 |
| 3 | rSA11/NSP1* |
| 4 | rSA11/NSP1-FUnaG |

(*Contains genetic marker mutations in NSP1 segment)

| | |
|---|---|
| 1 | Mock |
| 2 | rSA11-g5* |
| 3 | rSA11-NSP1-FUnaG |

VP1 dimer

NoV capsid pT7/NSP3-P2A-3xFL/NoV P2 (1.7 kB)

pT7/NSP3-2A-3xFL/NoV P (2.2 kB)

pT7 NSP3-2A-3x FL NoV VP1 (2.9 kB)

Lanes:
1. wt
2. NSP3-P2A-3xFL/NoV P2
3. NSP3-P2A-3xFL/NoV P
4. NSP3-P2A-3xFL/NoV VP1

Lanes:
1. mock
2. wt
3. NSP3-P2A-3xFL/NoV P2
4. NSP3-P2A-3xFL/NoV P
5. NSP3-P2A-3xFL/NoV VP1

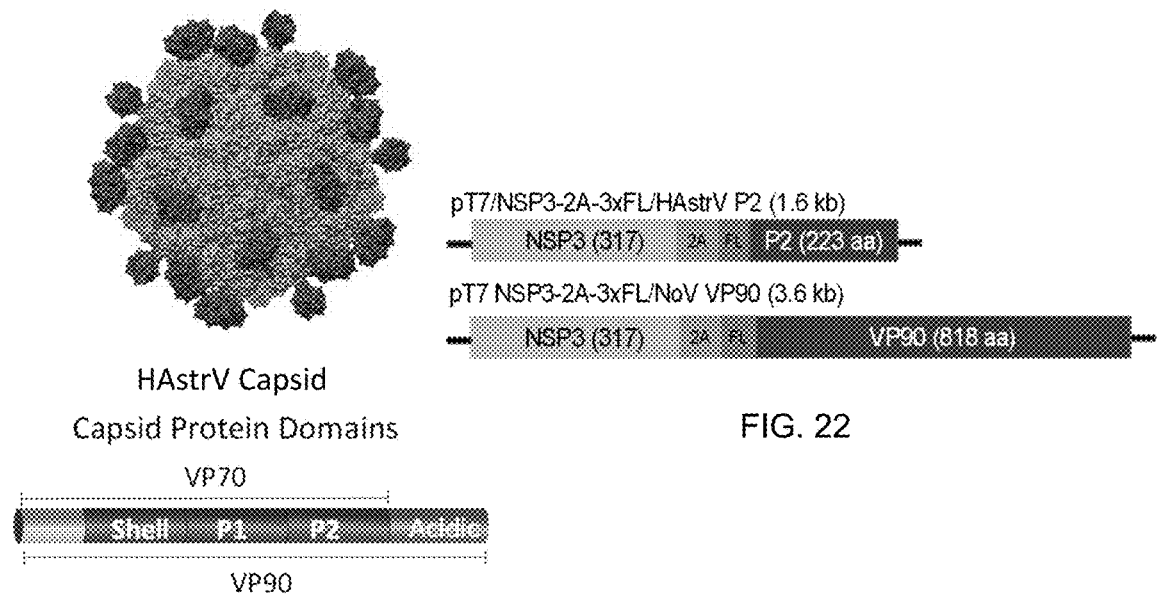
FIG. 21
FIG. 22
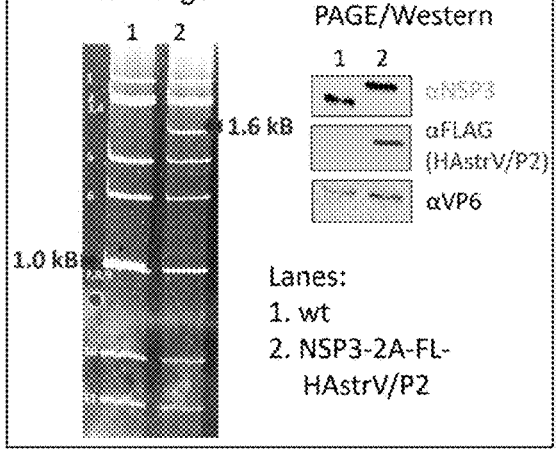
FIG. 23
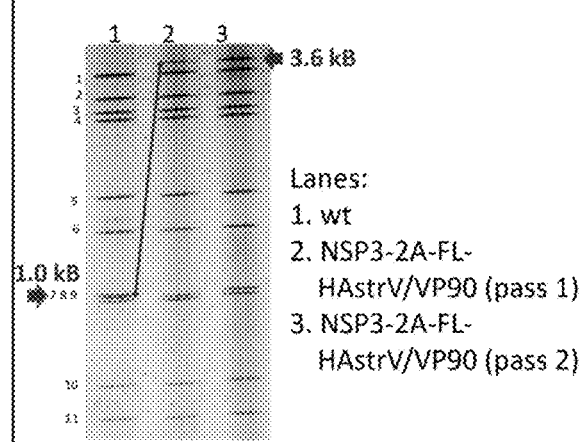
FIG. 24

SEQUENCE LISTING

```
<160> NUMBER OF SEQ ID NOS: 1

<210> SEQ ID NO 1
<211> LENGTH: 20
<212> TYPE: PRT
<213> ORGANISM: Sus scrofa

<400> SEQUENCE: 1

Ser Lys Phe Gln Ile Asp Lys Ile Leu Ile Ser Gly Asp Ile Glu Leu
1               5                   10                  15

Asn Pro Gly Pro
            20
```

RECOMBINANT ROTAVIRUS EXPRESSION SYSTEM AND RECOMBINANT ROTAVIRUSES

CROSS-REFERENCE TO RELATED APPLICATIONS

This application is the National Stage of International Patent Application No. PCT/US2019/41677, filed Jul. 12, 2019, which claims priority to U.S. Provisional Patent Application No. 62/697,869, filed Jul. 13, 2018, the contents of each of which are incorporated herein by reference in their entireties.

STATEMENT OF GOVERNMENTAL RIGHTS

This invention was made with Government support under grant AI131072 and AI144881 awarded by the National Institutes of Health (NIH). The Government has certain rights in this invention.

FIELD

Embodiments herein provide compositions, methods, uses and manufacturing procedures for rotavirus constructs and immunogenic compositions thereof. Some embodiments concern compositions that include, but are not limited to, chimeric rotaviruses of use in immunogenic compositions against rotavirus and an additional pathogenic virus infection in a subject. In certain embodiments, the rotavirus constructs are a part of a rotavirus expression system, the constructs including one or more nucleic acid molecules encoding one or more polypeptides of another pathogen (e.g. another enteric or mucosal pathogen).

SEQUENCE LISTING STATEMENT

The instant application contains a Sequence Listing which has been submitted via EFS-Web and is hereby incorporated by reference in its entirety. The ASCII copy, created on Jul. 12, 2019, is named IU-2018-137-02-WO_ST25, and is 562 bytes in size.

BACKGROUND

Rotaviruses and noroviruses are the leading causes of childhood gastroenteritis throughout the world. In the United States, as well as other countries where rotavirus vaccines are widely used, noroviruses are responsible for the majority of cases of acute gastroenteritis in children under the age of 5 years. Although noroviruses can cause disease in people of all ages, severity of this condition can be much worse in young children and the elderly. Based on a 2009 analysis of children in the US, noroviruses has been identified as responsible for an estimated 14,000 hospitalizations, 281,000 emergency department visits, and 627,000 outpatient visits, at a treatment cost of at least 273 million U.S. dollars annually. Globally, norovirus infections are estimated to cause more than 200,000 deaths each year (mostly of young children), while rotaviruses causes about 120,000 deaths in the same period. Although the mortality and morbidity associated with norovirus infections have driven extensive efforts to create norovirus vaccines, there are currently no norovirus vaccines commercially available.

SUMMARY

In a first example ("Example 1"), provided herein is a recombinant rotavirus expression system comprising: a nonstructural protein 3 (NSP3) expression vector including a nucleotide sequence encoding rotavirus (NSP3) and a nucleotide sequence encoding a non-rotavirus polypeptide, wherein the NSP3 and the non-rotavirus polypeptide are encoded by a single open reading frame, separated by a self-cleavage protease domain; a VP1 expression vector; a VP2 expression vector; a VP3 expression vector; a VP4 expression vector; a VP6 expression vector; a VP7 expression vector; a NSP1 expression vector; a NSP2 expression vector; a NSP4 expression vector; a NSP5/6 expression vector; and an African Swine Fever Virus NP868R RNA capping enzyme expression vector.

In a second example ("Example 2), provided herein is a recombinant rotavirus comprising a gene segment including a nucleotide sequence encoding rotavirus nonstructural protein 3 (NSP3) and a nucleotide sequence encoding a non-rotavirus polypeptide, wherein the NSP3 and the non-rotavirus polypeptide are encoded by a single open reading frame, separated by a self-cleavage protease domain.

In another example ("Example 3") further to Example 1, each of the NSP3 expression vector, VP1 expression vector, VP2 expression vector, VP3 expression vector, VP4 expression vector, VP6 expression vector, VP7 expression vector, NSP1 expression vector, NSP2 expression vector, NSP4 expression vector, and NSP5/6 expression vector are T7 expression vectors.

In another example ("Example 4") further to any of Examples 1-3, the self-cleavage protease domain is a 2A cleavage element.

In another example ("Example 5") further to any of Examples 1-4, the self-cleavage protease domain is a porcine teschovirus 2A (P2A) element.

In another example ("Example 6") further to any of Examples 1-5, the 2A element has a sequence having at least 80% sequence identity to SEQ ID NO: 1 (SKFQIDKILISGDIELNPGP).

In another example ("Example 7") further to any of Examples 1-6, the non-rotavirus polypeptide is derived from a virus that causes gastroenteritis.

In another example ("Example 8") further to any of Examples 1-7, the non-rotavirus polypeptide is derived from a virus selected from the group consisting of: norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

In another example ("Example 9") further to any of Examples 1-8, the non-rotavirus polypeptide induces an immunological response against a second virus that is not rotavirus.

In another example ("Example 10") further to any of Examples 1-9, the non-rotavirus polypeptide induces an immunological response against a virus selected from the group consisting of: norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

In another example ("Example 11") further to any of Examples 1-10, the non-rotavirus polypeptide is selected from the group consisting of norovirus VP1 protein, norovirus P domain, and norovirus P2 domain.

In another example ("Example 12") further to any of Examples 1-11, the rotavirus reverse genetics system or the recombinant rotavirus is based upon strain G1P [8].

In another example ("Example 13") further to any of Examples 1-12, a rotavirus expressible from the reverse genetics system is attenuated, or the recombinant rotavirus is attenuated.

In another aspect ("Example 14"), provided herein is a method for producing a recombinant rotavirus, the method comprising: transfecting BHK-T7 cells with the recombinant rotavirus expression system described herein; overseeding the transfected BHK-T7 cells with MA104 cells; preparing a clarified cell lysate; and isolating recombinant rotavirus.

In another example ("Example 15") further to Example 14, recombinant rotavirus is isolated by plaque purification.

In another example ("Example 16") further to Example 14 or 15, the recombinant rotavirus is attenuated.

Embodiments herein report compositions, methods, uses and manufacturing procedures for rotavirus constructs and immunogenic compositions thereof. Some embodiments concern compositions that include, but are not limited to, chimeric rotaviruses of use in immunogenic compositions against rotavirus infection as well as against other pathogenic virus infection in a subject. In certain embodiments, constructs of use herein can be generated and used where a rotavirus expression system further includes one or more nucleic acid molecules encoding one or more polypeptides of another pathogen (e.g. another enteric or mucosal pathogen).

Some embodiments disclosed herein can include a recombinant virus construct, including: at least one portion of a sequence encoding at least one genome segment of a first virus; at least one 2A element comprising a conserved Pro-Gly-Pro motif; and at least one portion of a sequence encoding at least one domain of a second virus. In certain embodiments, the first virus is a rotavirus. Consistent with these embodiments, the recombinant virus construct includes a NSP3 and/or NSP1 genome segment of a rotavirus. In some embodiments, a second virus can include at least one other genome segment from the same virus as the first virus or at least one genome segment from a separate rotavirus species and/or a virus other than a rotavirus that can cause gastroenteritis. In certain embodiments, the first virus can include at least one type of rotavirus and the second virus can include at least a segment of at least one other type of rotavirus that is different from the first virus. For example, the first virus can include at least one group A rotavirus and the second virus can include at least one non-group A rotavirus. In accordance with these embodiments, the second virus can include, but is not limited to, at least one virus including rotavirus, non-group A rotavirus, norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, coronavirus, or any combination thereof. In accordance with these embodiments, the at least one domain of the second virus can include, but is not limited to, VPO subunit, VP1 subunit, VP2 subunit, VP3 subunit, capsid protein, El-glyprotein protruding domain, protruding domain, outer capsid spike domain, head domain, SI capsid protein, penton, spike glycoprotein, or any combination thereof. In certain embodiments, the at least one 2A element can be located at a place downstream of the at least one portion of a sequence encoding at least one genome segment of a first virus and at a place upstream of at least one portion of a sequence encoding at least one domain of a second virus. In accordance with these embodiments, the virus construct expresses at least one genome segment, or a portion thereof, of the first virus and the at least one domain, or a portion thereof, of the second virus. In certain embodiments, the virus construct includes a rotavirus strain G1P [8].

In other embodiments, immunogenic compositions disclosed herein can include at least one recombinant rotavirus expressing at least one domain, or a portion thereof, of a second virus. In certain embodiments, the recombinant rotavirus is derived from any one of the recombinant virus construct disclosed herein. In some embodiments, the recombinant rotavirus can express at least a portion of norovirus capsid protein sufficient to induce immunogenic responses against a norovirus.

In other embodiments, compositions of the instant disclosure can include a composition that includes any one of the compositions disclosed herein and a pharmaceutically acceptable carrier or excipient. Alternatively, compositions of the instant disclosure can include an immunogenic composition that includes at least one recombinant rotavirus expressing at least one domain, or a portion thereof, of a second virus. The pharmaceutical compositions can be formulated for administration to the subject for delivery orally, subcutaneously, intramuscularly, intradermally, intranasally, topically, transdermally, parenterally, gastrointestinally, transbronchially, transalveolarly, and/or mucosally.

Certain embodiments herein concern compositions, methods and uses for inducing an immune response against one or more viruses can include, but are not limited to, rotaviruses and noroviruses in a subject, individually or simultaneously. In accordance with these embodiments, recombinant viruses are generated and can be used in immunogenic and/or vaccine compositions disclosed herein. Some embodiments relate to compositions, methods and uses for treating gastroenteritis or a condition associated with gastroenteritis. In accordance with these embodiments, methods disclosed herein can include methods for treating gastroenteritis or a condition associated with gastroenteritis in a subject by administering a therapeutically effective amount of a pharmaceutical composition disclosed herein. In any one of the embodiments disclosed herein, the subject can include a human and/or an animal such as a domesticated animal or livestock or other animal.

Yet other embodiments relate to a recombinant virus expression system for improved recombinant virus recovery. In accordance with these embodiments, the system can include, but is not limited to, at least one T7-transcription vector including any one of the recombinant virus constructs disclosed herein; one or more T7-transcription vectors, each corresponding to a single genome segment of a rotavirus; and at least one vector expressing African Swine Fever Virus NP868R RNA capping enzyme; wherein the recombinant virus expression system does not include any vectors expressing vaccinia virus DIR and D12L RNA capping enzymes.

Certain embodiments relate to a method of producing a recombinant rotavirus, comprising: transfecting BHK-T7 cells with the recombinant virus expression system disclosed in the instant application; overseeding the transfected BHK-T7 cells with MA104 cells; producing BHK-T7/MA104 cell lysates; transfecting MA104 monolayers; and producing a recombinant rotavirus.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

Figure 1:
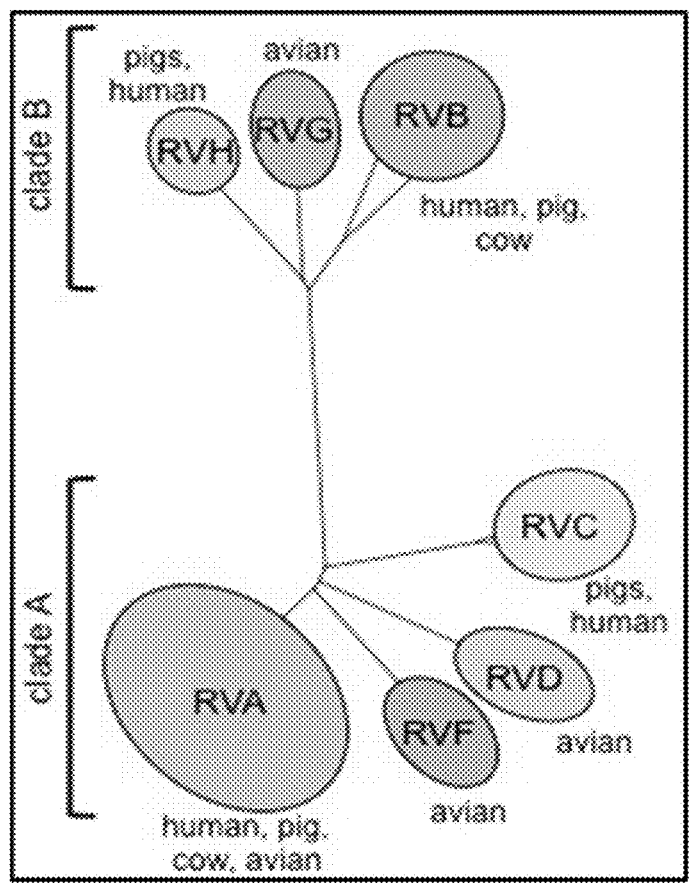
FIG. 1 represents a phylogenetic tree of rotavirus species. RVA is the major cause of rotavirus illness in humans.
Figure 2:
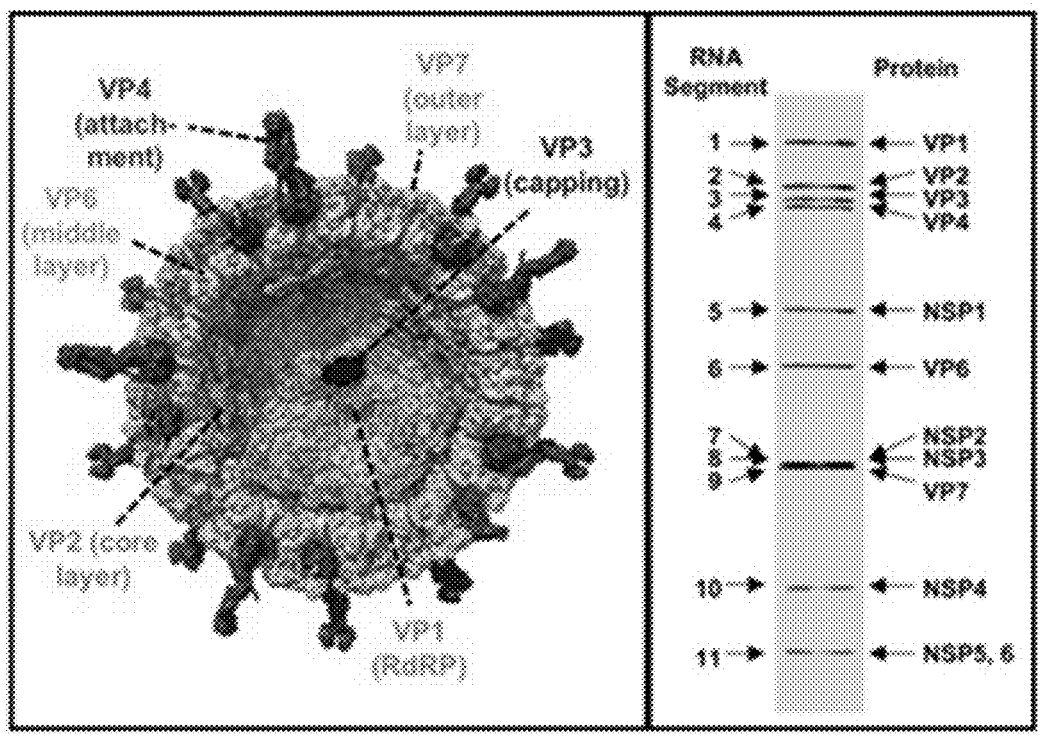
FIG. 2 represents rotavirus capsid with structural proteins labeled (Left) and dsRNA genome segments showing protein products (Right).
Figure 3:
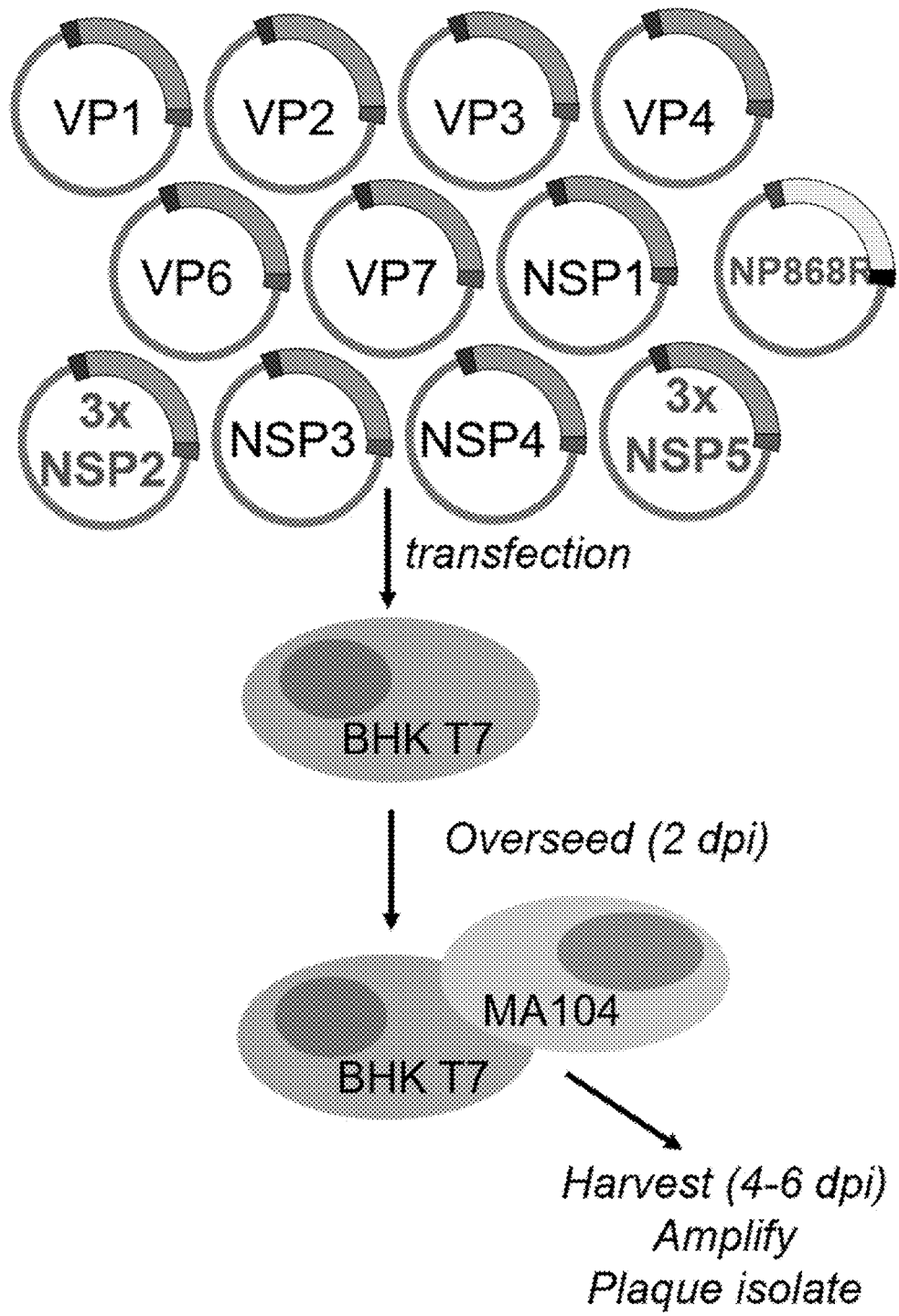

FIG. 3 represents a schematic drawing illustrating transfection of BHK-T7 cells with vectors for rotavirus (+) RNAs, a CMV vector for ASFV NP868R, and a pCAG vector for p10FAST. Briefly, three days after transfection, BHK-T7 cells are overseeded with MA104 cells in trypsin-containing media. The combined BHK-T7/MA104 cultures are harvested six days post transfection, and recombinant virus amplified by passage in MA104 cells.

FIG. 4 represents (A) a diagram illustrating the ASFV NP868R gene that was synthesized by Genewiz and inserted in a pCMV plasmid downstream of the CMV promoter; (B) a Polyacrylamide gel electrophoresis (PAGE) illustrating the electrophoretic profile for recombinant SA11 rotavirus (rSA11) and SA11-4F virus; (C) a bar graph illustrating fold increase in the level of virus recovered in RG experiments expressing ASFV NP868R capping enzyme compared to RG experiments expressing vaccinia virus capping DIR/D12L enzymes.

FIG. 5A represents (A) a schematic drawing illustrating modification of the SA11 pT7 NSP1 vector. The SA11 pT7 NSP1 vector was modified, removing a PacI site (NSP1*) or inserting an in-frame 3×Flag-tagged UnaG ORF (NSP1-FUnaG).

FIG. 5B represents (B) organization of the pT7-rSA11/NSP1-FUnaG plasmid.

FIG. 5C represents (C) genome segments of SA11-4F and RG-generated recombinant viruses, resolved by PAGE. Arrows identify NSP1 segments.

FIG. 5D represents (D) epifluorescence of MA104 cells infected with recombinant SA11 virus expressing UnaG.

FIG. 5E represents (E) Western blot illustrating the detection of VP6, NSP3, and NSP1-FUnaG in mock and infected cells (8 hr p.i.) with VP6, NSP3, and Flag antibodies.

FIG. 6 represents a PAGE illustrating electropherotypes of wildtype SA11-4F and sister strain with gene 7 rearrangement (g7re).

FIG. 7 represents proteins encoded by group A (RVA) rotavirus gene 7 (NSP3seg) and group C (RVC) rotavirus gene 6 (NSP3-dsRBPseg). Self-cleavage site in RVC 2A is labeled.

FIG. 8 represents location of domains in the norovirus capsid protein VP1. Shell(S), Protruding (P).

FIG. 9 represents organization of engineered NSP3seg dsRNAs introduced into recombinant SA11 rotavirus.

FIG. 10 represents (A) electropherotype; and (B) UnaG expression of recombinant SA11/NSP3-R2A/FUnaG virus.

FIG. 11 represents Western blot detection of VP6, NSP3, and UnaG in SA11 infected cells. Note efficient cleavage of NSP3-UnaG by P2A (lane 4) and poor cleavage by R2A.

FIG. 12 represents pT7/NSP3 plasmid design according to one embodiment.

FIG. 13 is a cartoon illustrating protein expressing from an modified pT7/NSP3 plasmid including a P2A element and a Flag-tagged fluorescent protein according to one embodiment.

FIG. 14 is a photograph of an RNA PAGE experiment conducted with the indicated plasmids. Gene 7 dsRNA is labeled with an arrow.

FIG. 15 is a photograph of a PAGE/Western blot run with the indicated plasmids.

FIG. 16 is a series of fluorescent micrographs of live cells transfected with the indicated plasmid.

FIG. 17 is a cartoon depicting the organization of the norovirus VP1 dimer (top) and the norovirus capsid.

FIG. 18 represents pT7/NSP3 plasmid design according to one embodiment.

FIG. 19 is a photograph of an RNA PAGE experiment conducted with the indicated plasmids. Gene 7 dsRNA is labeled with an arrow.

FIG. 20 is a photograph of a PAGE/Western blot run with the indicated plasmids.

FIG. 21 is a cartoon depicting human astrovirus (HAstrV) capsid (top) and the organization of the HAstrV CP90 capsid protein.

FIG. 22 represents pT7/NSP3 plasmid design according to one embodiment.

FIG. 23 is a photograph of an RNA PAGE experiment conducted with the indicated plasmids. Gene 7 dsRNA is labeled with an arrow.

FIG. 24 is a photograph of an RNA PAGE experiment conducted with the indicated plasmids. Gene 7 dsRNA is labeled with an arrow.

DEFINITIONS

As used herein, the singular form "a", "an", and "the" includes plural references unless indicated otherwise.

The term "treating" as used herein, unless explicitly stated or implied otherwise, includes administering to a human or an animal patient at least one dose of a pharmaceutical formulation. "Treating" includes lessening the likelihood and/or severity of at least one disease as well as limiting the length/duration of an illness, or the severity of an illness, or inducing a protective immune response. Treating a patient may or may not result in a cure of the disease or condition. The term "treating" refers to partially or completely alleviating, ameliorating, delaying onset of, improving, inhibiting progression of, relieving, and/or reducing incidence of one or more symptoms or causes of a particular disease, disorder or condition. The term also refers to inhibiting infection in a patient. Treatment may be administered to a subject who does not exhibit signs of a disease, disorder, and/or condition, and/or to a subject who exhibits only early signs of a disease, disorder, and/or condition for the purpose of decreasing the risk of developing pathology associated with the disease, disorder, and/or condition.

As used herein, unless explicitly stated otherwise or clearly implied the terms "therapeutically effective dose," "therapeutically effective amounts," "effective dose" and the like, refer to any amount of a recombinant rotavirus that has a net positive effect on health and well being of a human or other animal. Therapeutic effects may include an improvement in longevity, quality of life and the like, and may also include a reduced susceptibility to developing a disease, disorder, and/or condition, or slow or prevent deteriorating health or well being. The effects may be immediately realized after a single dose and/or treatment or they may be cumulatively realized after a series of doses and/or treatments. A "therapeutically effective amount" or "effective amount" in general means any amount that, when administered to a subject or animal for treating a disease, is sufficient to affect the desired degree of treatment for the disease, disorder, and/or condition at a reasonable benefit/risk ratio applicable to medical treatment. The specific therapeutically effective dose for any particular patient can depend upon a variety of factors including the disorder being inhibited, virulence of the specific recombinant rotavirus employed; the specific pharmaceutical composition employed; the age, body weight, general health, sex and diet of the patient; the time of administration, and route of administration; the duration of the treatment; and like factors well-known in the medical arts.

Pharmaceutical formulations described herein may be suitable for oral, parenteral (including subcutaneous, intradermal, intramuscular and intravenous) and/or rectal administration. The formulations may be presented in unit dosage form and may be prepared by any of the methods well known in the art of pharmacy. All methods include the step of bringing into association the active ingredient (i.e., a recombinant rotavirus of the present disclosure) with the carrier. In general, the formulations are prepared by uniformly and intimately bringing into association the active ingredient with a liquid carrier or, a finely divided solid carrier or both, and then, if necessary, forming the associated mixture into the desired dosage form.

Pharmaceutical formulations of the present disclosure suitable for oral administration can be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The formulation can also be a bolus, electuary or paste.

Pharmaceutical formulations of the present disclosure suitable for parenteral administration can include aqueous and non-aqueous sterile injectable solutions, and may also include an adjuvant, an antioxidant; a buffer; a bacteriostat; a solution which renders the composition isotonic with the blood of the recipient; and aqueous and non-aqueous sterile suspensions which can contain, for example, a suspending agent and a thickening agent. The formulations can be presented in a single unit-dose or multi-dose containers, and can be stored in a lyophilized condition requiring the addition of a sterile liquid carrier prior to use.

The term "pharmaceutically acceptable carrier or excipient", unless stated or implied otherwise, can be used herein to describe any ingredient other than the active component(s) that can be included in a formulation (e.g., carriers and adjuvants). The choice of carrier and/or adjuvant will to a large extent depend on factors such as the particular mode of administration, the effect of the carrier on solubility and stability, and the nature of the dosage form.

Unless explicitly stated otherwise or clearly implied otherwise, the term "immunogenic composition" can be used to refer to a composition (e.g., a pharmaceutical formulation) that induces an immune response in a subject when introduced to the subject; for example, a vaccine.

DETAILED DESCRIPTION

Embodiments herein provide compositions, methods, uses and manufacturing procedures for recombinant rotaviruses and immunogenic compositions thereof. Some embodiments concern compositions that include, but are not limited to, chimeric rotaviruses of use in immunogenic compositions against rotavirus infection and at least one additional pathogenic virus infection in a subject. In certain embodiments, recombinant rotaviruses are generated using a rotavirus reverse genetics system that includes an expression vector encoding rotavirus NSP3 and one or more polypeptides of another pathogen (e.g. another enteric or mucosal pathogen).

In a first aspect, provide herein is a recombinant rotavirus expression system rotavirus reverse genetics system. Kanai et al. developed a plasmid-based reverse genetics (RG) system that allows for genetic modification of any of the 11 dsRNA genome segments of simian rotavirus SA11. Kanai et al., Entirely plasmid-based reverse genetics system for rotaviruses, PROC NATL ACAD SCI USA 2017; 114 (9): 2349-2354 The Kanai RG system includes eleven SA11 T7 transcription vectors and three CMV support vectors-two expressing vaccinia virus DIR and D12L RNA capping enzymes and one expressing reovirus p10FAST fusion protein While Kanai et al. and additional studies have generated recombinant rotaviruses that express fluorescent proteins (FPs) by inserting report genes into the NSP1 open reading frame (ORF) of genome segment 5, NSP1 is expressed at low levels in infected cells and is subject to proteasomal degradation. This makes viruses expressing FP-fused NSP1 less than an ideal probe of rotavirus biology. Moreover, FPs were inserted into segment 5 in such a way that it compromised the NSP1 ORF, affecting the protein's function as an interferon antagonist affecting viral growth and pathogenesis. Described herein is a rotavirus recombinant rotavirus expression system in which rotavirus genome segment 7, which encodes NSP3, is modified.

In certain embodiments, the recombinant rotavirus expression system comprises a nonstructural protein 3 (NSP3) expression vector including a nucleotide sequence encoding rotavirus (NSP3) and a nucleotide sequence encoding a non-rotavirus polypeptide, wherein the NSP3 and the non-rotavirus polypeptide are encoded by a single open reading frame, separated by a self-cleavage protease domain; a VP1 expression vector; a VP2 expression vector; a VP3 expression vector; a VP4 expression vector; a VP6 expression vector; a VP7 expression vector; a NSP1 expression vector; a NSP2 expression vector; a NSP4 expression vector; a NSP5/6 expression vector; and an African Swine Fever Virus (ASFV) NP868R RNA capping enzyme expression vector. This simplified rotavirus expression system, which replaces the vaccinia DIR/D12L support vectors of the Kanai system with the ASFV NP868R expression vector enhanced recovery of recombinant virus by about 10-fold (see Examples section). Further, unlike previous systems relying on modification of segment 5, modification of segment 7 did not result in interruption or deletion of any portion of the segment's ORF.

The expression vectors used to express VP1-VP4, VP6-VP7, NSP1-NSP5/6, and ASFV NP868R RNA capping enzyme can be any appropriate expression vector capable of expression in a selected cell line. In some embodiments, BHK-T7 cells are transfected with the recombinant rotavirus expression system, and thus the expression vectors used to express VP1-VP4, VP6-VP7, NSP1-NSP5/6 are T7 expression vectors. In some embodiments, the expression vector used to express ASFV NP868R RNA capping enzyme is a CMV expression vector.

The self-protease domain is between the NSP3 polypeptide and the non-rotavirus polypeptide, so that NSP3 and the non-rotavirus polypeptide are automatically separated during translation. That is, the self-cleavage protease domain separates NSP3 from the non-rotavirus polypeptide.

In certain embodiments, the self-cleavage protease domain is a 2A cleavage element. Many viruses use 2A 'self-cleavage' elements to generate more than one protein from a single ORF. 2A elements are roughly 20 amino acids in length and end with a conserved Pro-Gly-Pro motif. During translation of the 2A element, the ribosome fails to form a peptide bond between the Gly-Pro residues, thus disconnecting the protein product synthesized upstream of the residues from any protein product synthesized downstream of the residues. The presence of a 2A element causes the upstream protein to end with a few extra 2A-derived residues and the downstream polypeptide to start with a Pro residue. In particular embodiments, the self-cleavage protease is a porcine teschovirus 2A (P2A) element. The 2A element has the sequence SKFQIDKILISGDIELNPGP (SEQ ID NO: 1). In some embodiments the 2A element has a sequence having at least 80%, at least 85%, at least 90%, at least 95%, at least 98%, at least 99%, or 100% sequence identity to SEQ ID NO: 1.

In some embodiments, the non-rotavirus polypeptide is derived from a virus that causes gastroenteritis. As used herein, "derived" means that the non-rotavirus polypeptide originated from a virus other than rotavirus. For example, the non-rotavirus polypeptide can be derived from norovirus, and can be, for example, norovirus VP1, norovirus P domain, or norovirus P2 domain.

In certain embodiments, the virus that causes gastroenteritis is selected from norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

In particular embodiments, the non-rotavirus polypeptide is capable of inducing an immunological response against the virus from which it originated (i.e., a second virus that is not rotavirus). In such embodiments, a resulting recombinant rotavirus expresses both the rotavirus polypeptides and the non-rotavirus polypeptide, allowing the recombinant rotavirus to be used as a dual vaccine, eliciting protective immune responses to both the rotavirus and the second virus (i.e., source of the non-rotavirus polypeptide).

In certain embodiments, the non-rotavirus polypeptide induces an immunological response against one of norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

In some embodiments, the recombinant rotavirus expression system is based upon rotavirus strain G1P [8]. That is, one or more of the rotavirus gene segments (i.e., VP1-VP4, VP6-VP7 segments and NSP1-NSP5/6 segments) are from strain G1P [8]. In some embodiments, the recombinant rotavirus expression system includes gene segments from two or more viral strains, resulting in a reassortant virus. For example, in some embodiments, at least one of the gene segments is a human G1P [8] strain gene segment, and at least one of the gene segments is a simian SA11 strain gene segment. In other embodiments, all rotavirus gene segments of the recombinant rotavirus expressions system are G1P [8] strain gene segments.

In some embodiments, the recombinant rotavirus expression system and expressed recombinant rotaviruses can be tailored for use in, for example, humans, livestock, or poultry. Using a particular rotavirus strain as the basis for the expression system or recombinant virus, or two or more rotavirus strains to produce a reassortant virus, a recombinant rotavirus expression system and the resulting recombinant rotaviruses can be tailed for use in a desired species.

In another aspect, provided herein are recombinant rotaviruses obtainable from the recombinant rotavirus expression systems described herein. In some embodiments, recombinant rotaviruses obtainable from the recombinant rotavirus expression systems described herein express all rotavirus proteins in their entirety in addition to the non-rotavirus polypeptide. As provided above, in some embodiments the non-rotavirus polypeptide can induce an immune response to a virus other than rotavirus. In this regard, the recombinant rotavirus can confer dual immunity to two different viruses simultaneously.

As the recombinant rotavirus is obtained from the described recombinant rotavirus expression systems, it will necessarily include a nucleotide sequence encoding rotavirus nonstructural protein 3 (NSP3) and a nucleotide sequence encoding a non-rotavirus polypeptide, wherein the NSP3 and the non-rotavirus polypeptide are encoded by a single open reading frame, separated by a self-cleavage protease domain. The details of these elements are provided above in relation to the recombinant rotavirus expression systems.

In some embodiments, the recombinant rotavirus is attenuated. Attenuated rotavirus strains are known, such as attenuated G1P [8]. Thus, in some embodiments, recombinant rotavirus expression systems and the resulting recombinant rotavirus can be based on an attenuated strain.

In another aspect, provided herein are immunogenic compositions comprising a recombinant rotavirus described herein. Immunogenic compositions may further comprise, for example a pharmaceutically acceptable excipient. The immunogenic compositions can be formulated for administration to the subject for delivery orally, subcutaneously, intramuscularly, intradermally, intranasally, topically, transdermally, parenterally, gastrointestinally, transbronchially, transalveolarly, or mucosally. In some embodiments, immunogenic compositions are formulated for oral, subcutaneous, or intramuscular administration.

In another aspect, provided herein are methods for inducing a protective immune response against rotavirus and a second virus in a subject. In some embodiments, such a method includes administering an effective amount an immunogenic composition described above to the subject. In some embodiments, the second virus is one of norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus In another aspect, provided herein are methods for producing a recombinant rotavirus. In certain embodiments, such methods include transfecting BHK-T7 cells with the recombinant rotavirus expression system described herein; overseeding the transfected BHK-T7 cells with MA104 cells; preparing a clarified cell lysate; and isolating recombinant rotavirus. In some embodiments, plasmid mixtures used for transfecting BHK-T7 cells include 1× levels of plasmid vectors encoding VP1-VP4, VP6-VP7, NSP1, NSP3, and NSP4, and about 3× levels or higher of plasmid vectors encoding NSP2 and NSP5. Transfected BHK-T7 cells are overseeded with MA104 cells to promote amplification of the recombinant rotavirus. Consistent with these embodiments, the method may further include the step of freeze-thawing the BHK-T7/MA104 cell cultures. For example, following amplification of the recombinant rotavirus in BHK-T7/MA104 cells, the cells may be freeze-thawed three times. In some embodiments, cells are centrifuged at low speed to remove large debris. In certain embodiments, recombinant viruses in cell lysates are amplified by passage in MA104 cells, plaque isolated, and amplified again in MA104 cells.

In some embodiments, the recombinant rotavirus is isolated by plaque purification. In certain embodiments, the produced recombinant rotavirus is attenuated.

In another aspect, provided herein is a recombinant virus construct, comprising: at least one portion of a sequence encoding at least one genome segment of a first virus; at least one 2A element comprising a conserved Pro-Gly-Pro motif; and at least one portion of a sequence encoding at least one domain of a second virus. In certain embodiments, the first virus is a rotavirus.

In certain embodiments, the recombinant virus construct includes at least one genome segment of the first virus comprising at least one nonstructural protein genome segment selected from NSP1, NSP2, NSP3, NSP4, NSP5, and NSP6 genome segments; and/or at least one structural protein genome segment selected from VP1, VP2, VP3, VP4, VP6, and VP7 genome segments. Consistent with these embodiments, the recombinant virus construct can include a NSP3 and/or NSP1 genome segment of a rotavirus.

Some embodiments provide a dual vaccine that protects against two different types of virus. Consistent with these embodiments, the second virus can be the same virus as the first virus and/or a virus other than a rotavirus that can cause gastroenteritis. In certain embodiments, the first virus can include at least one type of rotavirus and the second virus can include at least one other type of rotavirus that is different from the first virus. For example, the first virus can include at least one group A rotavirus (or a portion thereof) and the second virus can include at least one non-group A rotavirus (or a portion thereof). In some embodiments, the second virus can include, but is not limited to, at least one virus comprising rotavirus, non-group A rotavirus, norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, coronavirus, or any combination thereof. In accordance with these embodiments, the at least one domain of the second virus can include, but is not limited to, VPO subunit, VP1 subunit, VP2 subunit, VP3 subunit, VP4 subdomains, capsid protein, El-glyprotein protruding domain, protruding domain, outer capsid spike domain, head domain, S1 capsid protein, penton, spike glycoprotein, or any combination thereof. In other embodiments, the second virus can be an enteric virus other than a rotavirus capable of causing gastroenteritis in a subject.

In some embodiments, the at least one 2A element can be located at a place downstream of the at least one portion of a sequence encoding at least one genome segment of a first virus and at a place upstream of at least one portion of a sequence encoding at least one domain of a second virus. In certain embodiments, the at least one 2A element can comprise a sequence having 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to SEQ ID NO: 1 (SKFQIDKILISGDIELNPGP). In accordance with these embodiments, the virus construct expresses at least one genome segment, or a portion thereof, of the first virus and the at least one domain, or a portion thereof, of the second virus. In certain embodiments, the virus construct can include, but is not limited to, a live, attenuated rotavirus or a rotavirus strain G1P [8].

In any one of the embodiments disclosed herein, the rotavirus comprises at least one rotavirus from group A rotaviruses (RVA).

Rotavirus, a genus in the Reoviridae family of segmented dsRNA viruses, has been resolved into eight species (RVA-RVH) (see for example FIG. 1). The RVA represents a large genetically diverse group of rapidly evolving viruses that are primary causes of severe diarrhea in young children throughout the world. RVA infections lead to >200,000 deaths each year, most occurring in Africa and Asia. Several developed countries, including the US, have introduced rotavirus vaccines into their childhood immunization programs.

Two highly effective rotavirus vaccines [ROTARIX® (GSK) and ROTATEQ® (Merck)] are in widespread use in the US and other countries. Both vaccines consist of live attenuated strains of rotaviruses and are orally administered to infants at 2 and 4 (ROTARIX®) or 2, 4, and 6 (ROTATEQ®) months of age. While ROTATEQ® is formulated from five bovine-human reassortant strains of rotavirus, ROTARIX® is composed of a single human rotavirus isolate (genotype G1P [8]) rendered attenuated by extensive serial passage in cell culture. G1P [8] rotaviruses are the most common cause of rotavirus disease in children, and ROTARIX® provides cross protection against human rotaviruses of other genotypes. ROTARIX® causes a limited asymptomatic intestinal infection in vaccines, inducing immunological protective responses that are likely to include the production of neutralizing secretory IgA antibodies.

Referring now to FIG. 2, rotaviruses have a non-enveloped icosahedral capsid that encloses a genome consisting of 11 segments of double-stranded (ds) RNA. The G and P genotypes of rotavirus isolates are defined by the outer capsid proteins VP7 (glycoprotein) and VP4 (protease-sensitive attachment protein), respectively. The rotavirus genome segments are mostly monocistronic, containing a single open-reading-frame (ORF) that encodes a structural protein (VP1-VP4, VP6-VP7) or nonstructural protein (NSP1-NSP6). Two of the nonstructural proteins, the interferon antagonist NSP1 and translation regulator NSP3, are not essential for virus replication in cell culture; however, these proteins can affect progeny yields. During rotavirus genome replication, viral (+) RNAs not only direct protein synthesis but also act as templates for dsRNA synthesis. Segment 5 encodes the interferon antagonist NSP1, a non-essential viral protein. Others have used RG systems to generate recombinant rotaviruses with modified segment 5 RNAs that express truncated NSP1 and GFP and UnaG reporter proteins. With this system, recombinant SA11 viruses have been made in which the ORF of segNSP1 has been partially deleted and replaced with a foreign reporter protein (eGFP or mCherry). However, no recombinant rotaviruses have been reported that express a foreign protein, without sacrificing the coding potential of one of the viral ORFs.

Similar to rotaviruses, noroviruses are also the leading causes of childhood gastroenteritis throughout the world. In the US and other countries where rotavirus vaccines are widely used, noroviruses are responsible for the majority of cases of acute gastroenteritis in children under 5 years of age. Although noroviruses can cause disease in people of all ages, severity is greatest in the young and the elderly. Based on an analysis of 2009 data for US children, noroviruses are responsible for an estimated 14,000 hospitalizations, 281,000 emergency department visits, and 627,000 outpatient visits, at a treatment cost of at least $273 million each year. Globally, norovirus infections are estimated to cause more than 200,000 deaths each year (mostly of children), with rotaviruses causing approximately 120,000. Although the mortality and morbidity associated with norovirus infections have driven extensive efforts to create norovirus vaccines, none is yet commercially available.

EXAMPLES

Kanai et al., Entirely plasmid-based reverse genetics system for rotaviruses, PROC NATL ACAD SCI USA 2017; 114 (9): 2349-2354, developed a plasmid-based reverse genetics (RG) system that allows genetic modification of any of the 11 dsRNA genome segments of simian rotavirus SA11. The RG system includes eleven SA11 T7 transcription vectors and three CMV support vectors-two expressing vaccinia virus D1R and D12L RNA capping enzymes and one expressing reovirus p10FAST fusion protein.

To enhance the recovery of recombinant virus by the RG system, the capping-enzyme gene of African swine fever virus (ASFV) NP868R, a protein with triphosphatase, guanylyltransferase, and methyltransferase activities was synthesized. Then, the two support vectors expressing vaccinia virus D1R/D12L were replaced with a single vector expressing the African Swine Fever Virus (ASFV) NP868R RNA capping enzyme. Accordingly, the modified RG system contains eleven (pT7) T7-promoter plasmids expressing SA11 (+) RNAs, a CMV-promoter plasmid expressing the AFSV NP868R capping enzyme, and a pCAG vector expressing p10FAST fusion protein. Referring now to FIG. 3, in this modified rotavirus RG system, baby hamster kidney cells expressing T7 polymerase (BHK-T7) are transfected with T7 vectors for rotavirus (+) RNAs, a CMV vector for ASFV NP868R, and a pCAG vector for p10FAST. Three days after transfection, BHK-T7 cells are overseeded with MA104 cells in trypsin-containing media. The combined BHK-T7/MA104 cultures are harvested six days post transfection, and recombinant virus amplified by passage in MA104 cells.

Figure 4A:
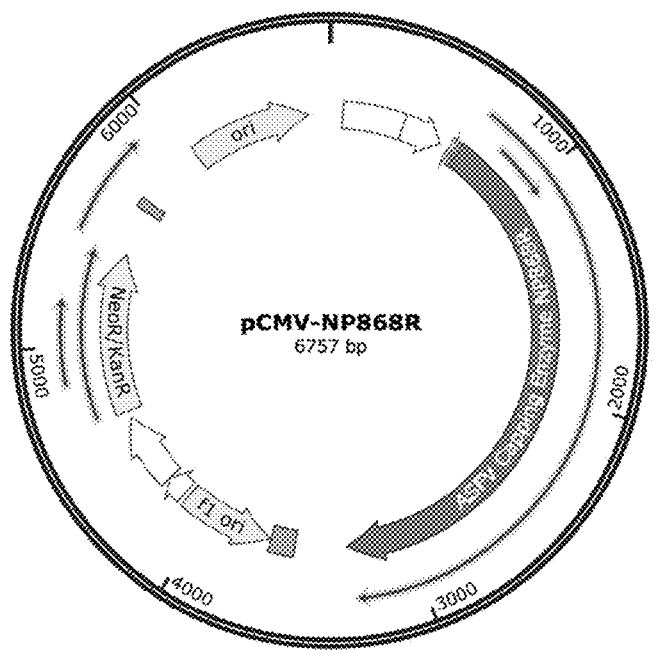
Figure 4B:
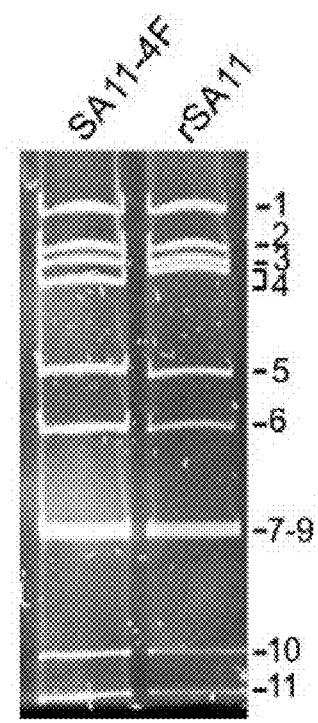
Figure 4C:
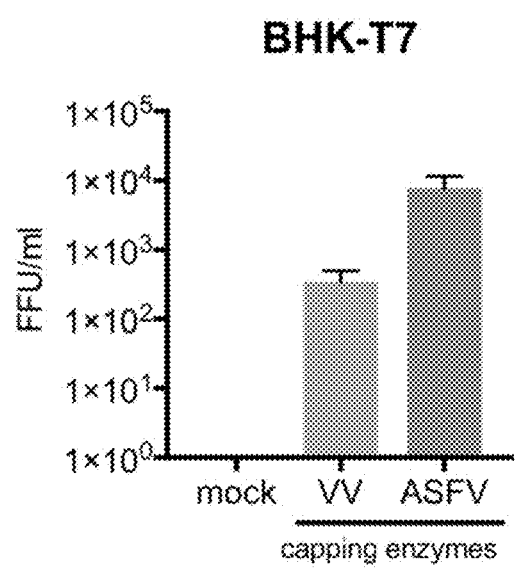

Referring now to FIG. 4, the experiments provided that replacing the D1R/D12L support vectors with an NP868R-expression vector enhanced recovery of recombinant virus from the rotavirus RG system. Approximately, about 10-fold more recombinant virus were recovered in RG experiments expressing ASFV NP868R capping enzyme than vaccinia virus capping D1R/D12L enzymes. (FIG. 4C). The modified RG system uses a single support plasmid (NP868R) in place of the originally described two support plasmids (vaccinia virus D1R & D12L) to generate capping activity. Therefore, the ASFV NP868R capping enzyme promotes greater recovery of recombinant virus than the vaccinia virus D1R and D12L capping enzymes.

Figures 5A, 6A:
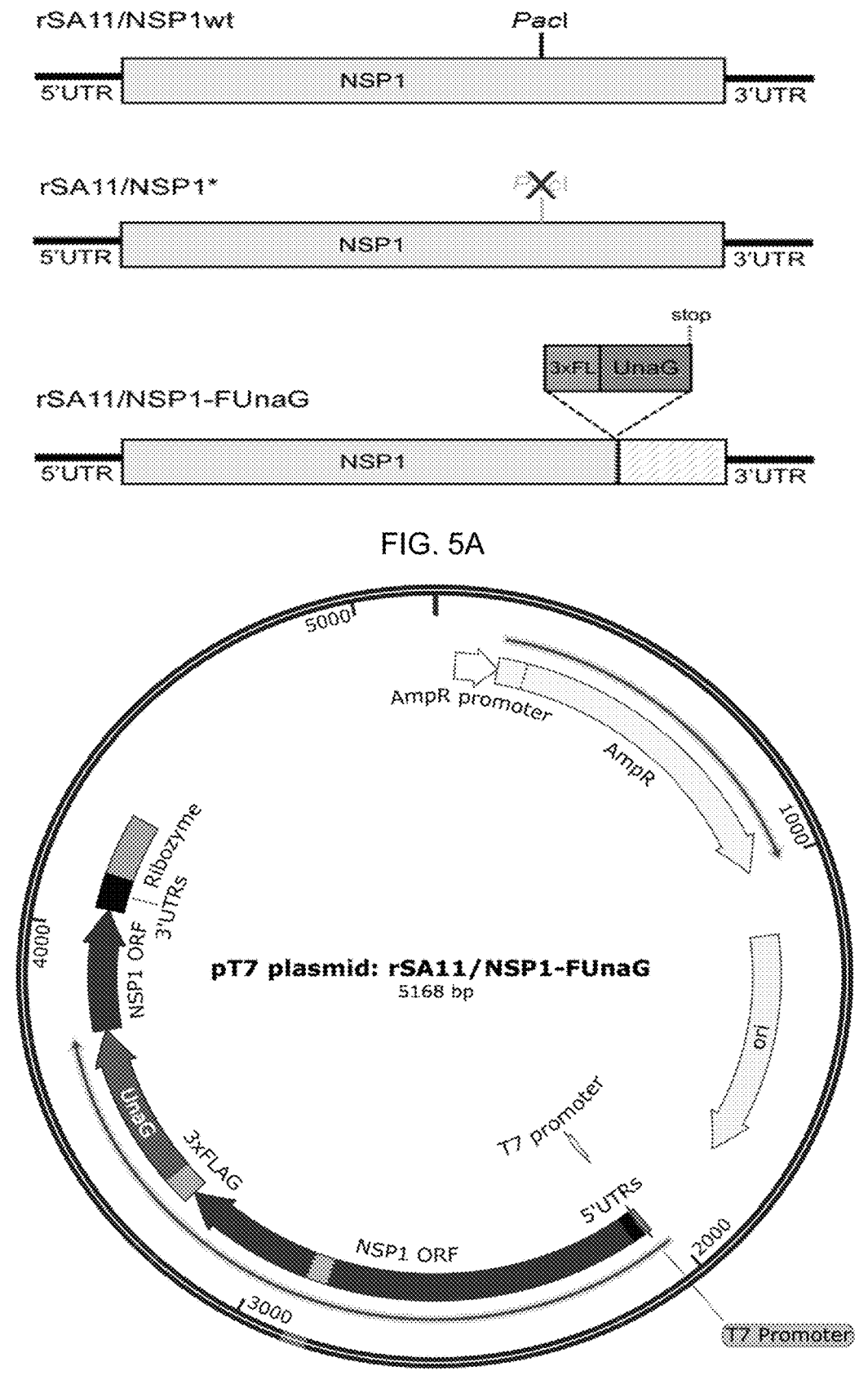

Referring now to FIG. 5, the SA11 pT7 NSP1 vector was modified by removing a PacI site (NSP1*) or inserting an in-frame 3×Flag-tagged UnaG ORF (NSP1-FUnaG) (FIG. 5A). Generation of a fusion protein NSP1-FUnaG was confirmed by Western blot assay with VP6, NSP3, and Flag antibodies (FIG. 5E).

Figure 6:
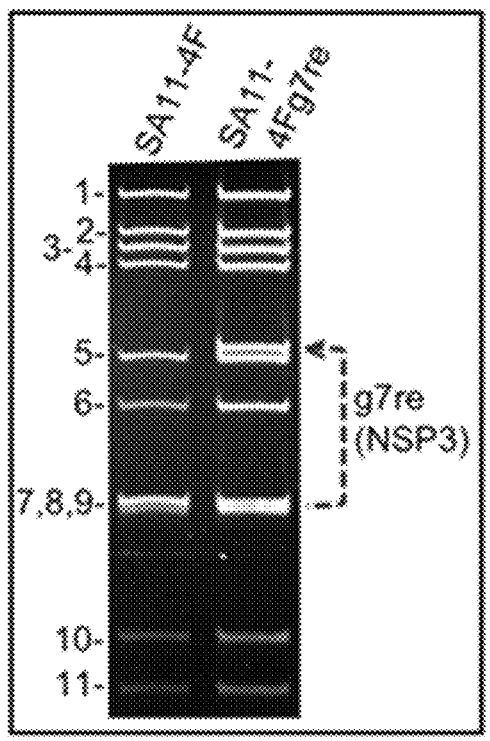

The collective size of the 11 rotavirus genome segments is about 18.5 kB. However, a number of naturally occurring rotavirus variants have been recovered with genomes that are significantly larger, in some cases approaching 20 kB. The increased size typically results from the introduction of sequence duplication within a genome segment, yielding viral variants that display unusual genome profiles upon gel electrophoresis (FIG. 6). The most commonly characterized rotavirus variants have sequence duplications in the segNSP1 and segNSP3 dsRNAs. The longest segNSP1 duplication described so far is about 1.2 kB. The longest segNSP3 duplication is about 0.9 kB, yielding an atypical genome segment with a size of about 2.0 KB instead of its wild type about 1.1 kB size. Notably, rotavirus variants are genetically stable and, in general, grow about as well as wildtype viruses. It is also possible to use RG systems to create genetically stable recombinant rotaviruses that maintain sequence duplications. Accordingly, the ability of rotaviruses to carry extra genetic information of greater than 1 kB suggests that it is possible to re-engineer the virus to produce a foreign protein that is more than 300 amino acids in size.

Figure 7:
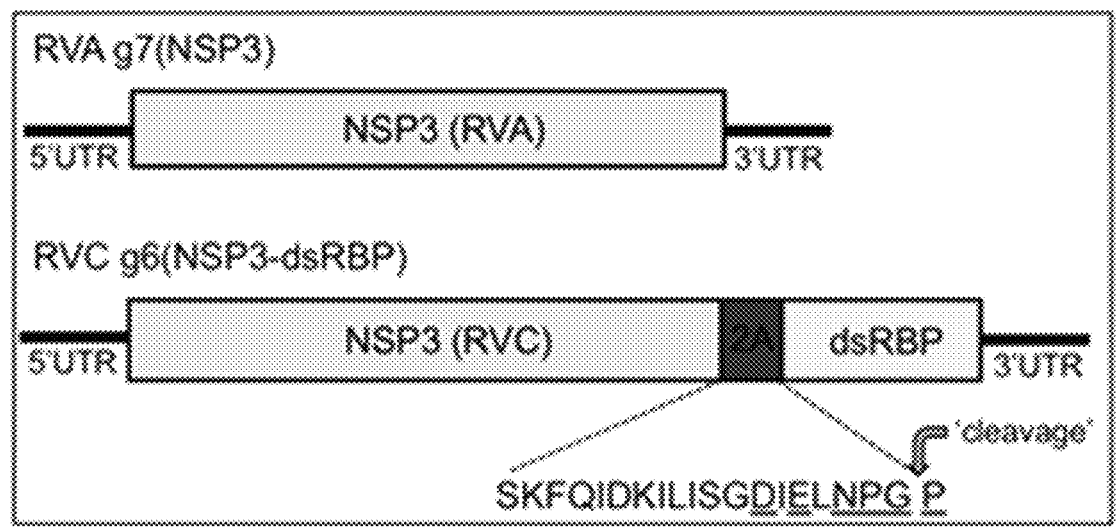

Many viruses use 2A 'self-cleavage' elements to generate more than one protein from a single ORF. 2A elements are roughly 20 amino acids in length and end with a conserved Pro-Gly-Pro motif. During translation of the 2A element, the ribosome fails to form a peptide bond between the Gly-Pro residues, thus disconnecting the protein product synthesized upstream of the residues from any protein product synthesized downstream of the residues. The presence of a 2A element causes the upstream protein to end with a few extra 2A-derived residues and the downstream polypeptide to start with a Pro residue. While group A rotaviruses, like those that formulate rotavirus vaccines, do not use 2A elements to produce viral proteins, group C rotaviruses do. In particular, the segNSP3 dsRNA of group C viruses contains an ORF that encodes an NSP3 protein that is functionally and structurally similar to RVA NSP3, but due to a downstream 2A element, also produces a second protein (dsRBP)—a double-strand RNA binding protein that inhibits protein kinase R (PKR) activation (FIG. 7). Based on the properties of the group C segNSP3 dsRNA, one can create group A rotaviruses with an analogous segNSP3 dsRNA (i.e., a rotavirus that expresses a functional NSP3 protein and, through downstream placement of a 2A element, a second foreign protein). There is precedence for using 2A elements to drive the expression of extra proteins for other members of the Reoviridae. For example, recombinant mammalian reoviruses have been generated with 2A elements that direct expression of the HIV gag protein and the eel epi fluorescence green protein (UnaG). More recently, recombinant rotaviruses have been described that contain re-engineered segNSP1 dsRNA, wherein the NSP1 ORF has been largely replaced with a 2A element fused to a fluorescent reporter protein. In the present disclosure, 2A self-cleavage elements were used to produce recombinant SA11 rotaviruses that express all 12 viral proteins plus an additional separate foreign protein.

Modified reverse genetics system. The plasmid-based rotavirus RG system developed by Kanai et al. relies on co-transfection of BHK-T7 cells with three types of plasmids: (1) eleven T7 transcription (pT7) vectors that direct the expression of the 11 rotavirus (+) RNAs; (2) two CMV-pol II plasmids that direct the expression of the vaccinia virus D1R and D12L RNA capping enzymes; and (3) a CMV-pol II plasmid that directs the expression of the avian reovirus p10FAST fusion protein. The system was inefficient leading us to make changes that improved the recovery of recombinant virus by at least 10-fold (FIG. 4). With the modified system, recombinant SA11 viruses with mutations in several genome segments (e.g., NSP1, NSP2, NSP3, and/or VP3) have been generated, including the mutations that significantly decrease the efficiency of virus replication. The major changes that were made to the RG system are replacing the two plasmids for the vaccinia virus capping enzyme complex with a single plasmid encoding the African swine fever virus (ASFV) NP868R capping enzyme and discontinuing use of the p10FAST plasmid. In this example, these results provide that a vector expressing p10FAST is no longer necessary for the modified reverse genetics system disclosed herein.

Figure 9:
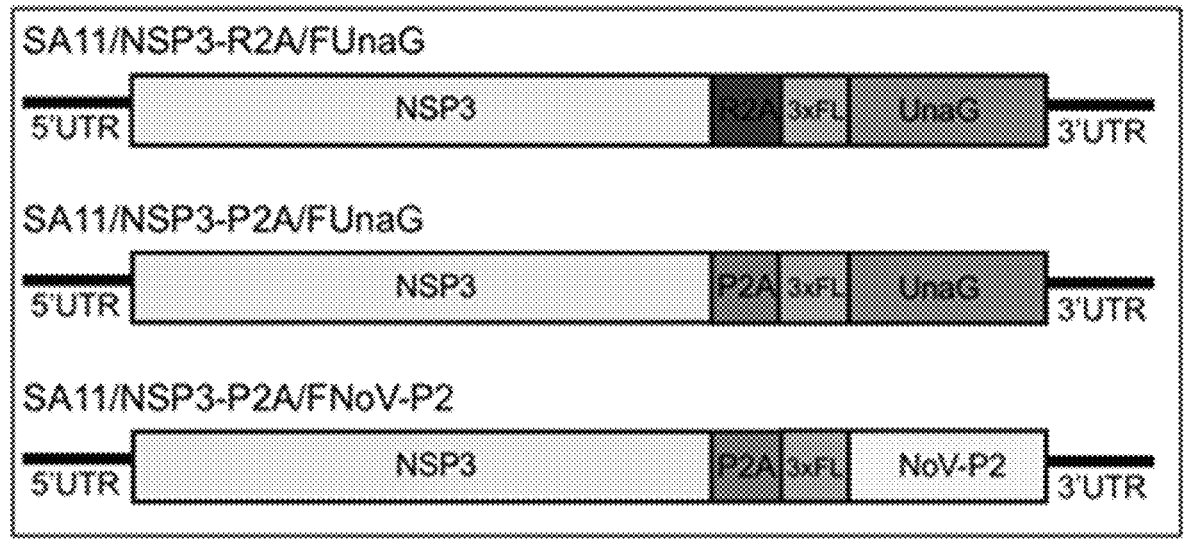
Figure 10:
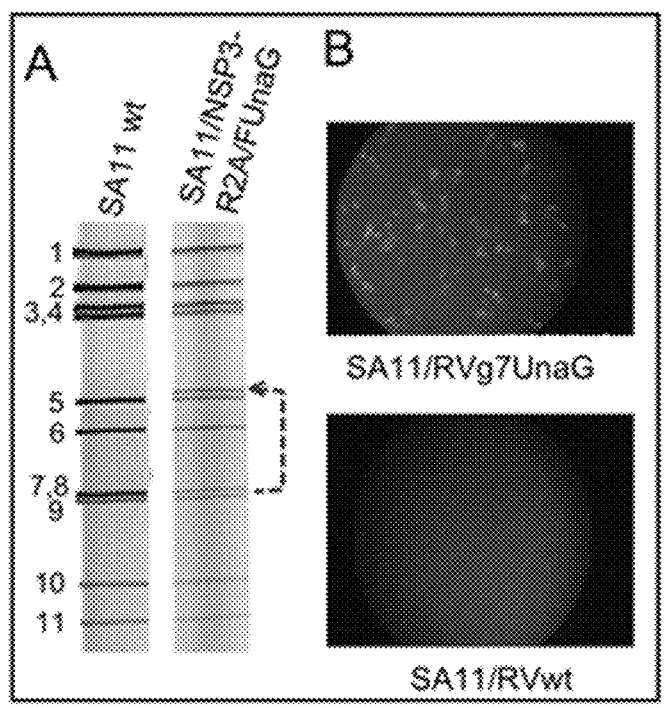
Figure 11:
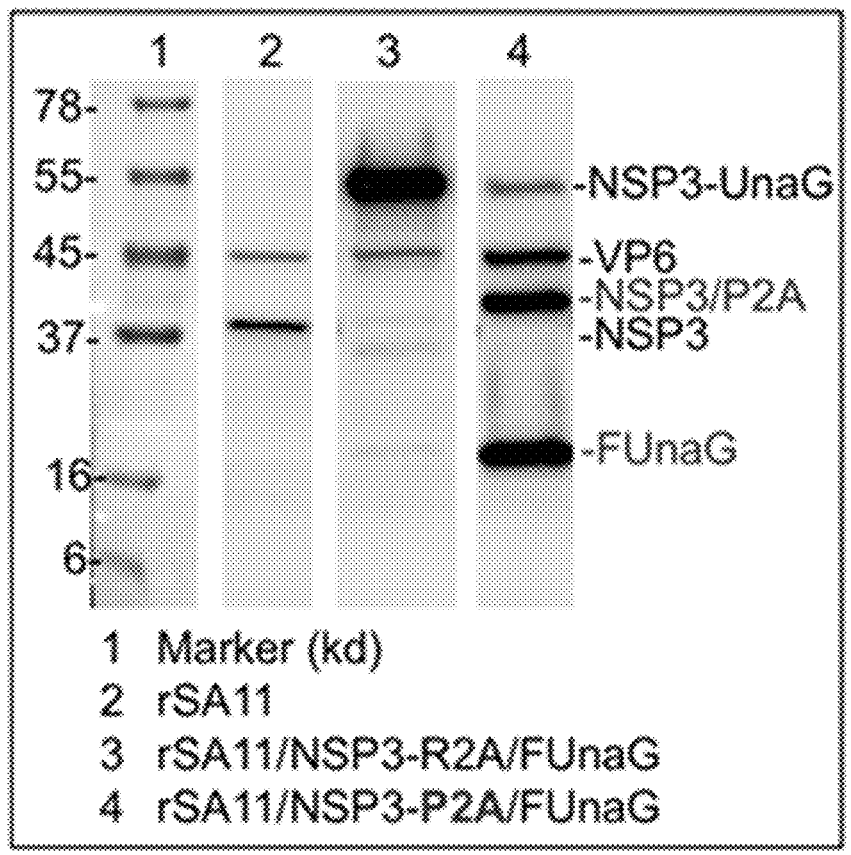

Recombinant SA11 viruses expressing UnaG. To investigate the possibility of using SA11 as an expression vector for a foreign protein, the possibility of creating recombinant viruses with a Flag-tagged (F) UnaG ORF inserted into either the segNSP1 or segNSP3 dsRNA was examined. The FUnaG ORF insertion in segNSP1 was placed in-frame about two-thirds of the way into the NSP1 ORF, and due to a stop codon at the end of the UnaG ORF, encoded a putative NSP1 (truncated)-FUnaG fusion protein. The FUnaG ORF was placed in segNSP3 downstream of the NSP3 ORF. Inserted in-between the NSP3 and FUnaG ORFs was an RVC 2A element (R2A) (FIG. 9). Recombinant SA11 viruses containing both types of UnaG insertions (confirmed by sequencing) and that expressed UnaG (confirmed based on epifluorescence and Western blot analysis) were recoverable (FIG. 10). Surprisingly, analysis of cells infected with recombinant virus containing segNSP3-R2A/FL/UnaG genome segment showed that while UnaG was expressed, the R2A element was poorly functioning (FIG. 11). As a result, most of the protein product from the genome segment represented NSP3 fused to UnaG.

Due to the poor performance of the R2A element in cleaving the NSP3 and FUnaG products of the segNSP3-R2A/FL/UnaG genome segment, the pT7 plasmid for the segNSP3 RNA was redesigned such that it contained a porcine teschovirus 2A (P2A) element instead of R2A (29). A GAG flexible linker was inserted in front of the P2A. Analysis of recombinant SA11 virus containing the segNSP3/P2A/FL/UnaG segment showed that it efficiently expressed NSP3 and UnaG as two separate proteins (FIG. 11). Less than 10% of the product of the segment represented NSP3-fused to UnaG, indicating that the P2A element functioned well. These results indicate that it is possibly to re-engineer the rotavirus genome, such that the virus can express its expected 12 viral proteins, plus a separate foreign protein.

Results illustrate that all recombinant viruses are genetically stable, retaining foreign sequences that are placed into their genomes. Also, the amount of FUnaG expressed by recombinant viruses containing a segNSP3-R2A/FL/UnaG segment is significantly greater than that of the segNSP1-R2A/FL/UnaG segment (normalized to expression of the inner capsid protein VP6). Without bound by any theory or limitation, this is probably expected given that, in infected cells, NSP3 is a moderately expressed viral protein, while NSP1 is expressed at much lower levels. The implications of this for vaccine purposes are that expression of a foreign protein through the segNSP3 is more likely to induce strong immunological responses than possible through the segNSP1. Further, any changes made to the segNSP1, including adding an R2A/UnaG cassette after the NP1 ORF, significantly reduced the efficiency of virus growth. This result suggests that the modifications are preventing NSP1 from suppressing interferon response, an activity of NSP1 known to be required for efficient virus replication. In contrast, recombinant viruses with segNSP3-R2A/FL/UnaG dsRNAs grew as well as wildtype virus, suggesting that such viruses can likely reach titers necessary for use as vaccine candidate strains.

Figure 8:
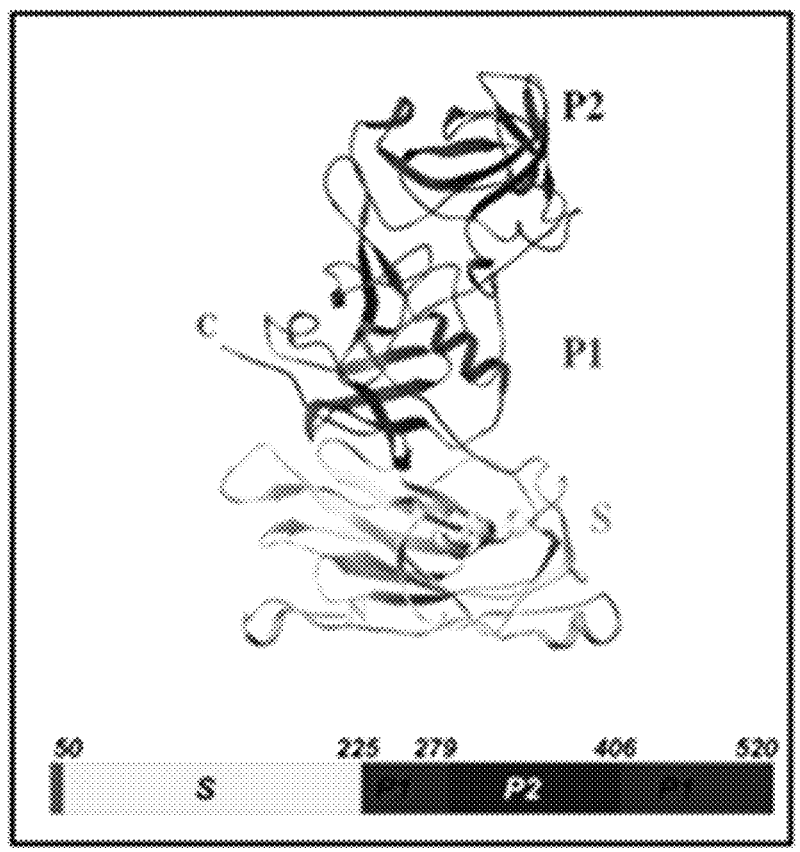

Noroviruses, members of the ('aliciviridae family, have small non-enveloped capsids that contain a positive-sense single-stranded RNA genome of about 7.5 kB. The development of human norovirus vaccines has been challenging given the absence of permissive cell lines and small animal models. Also problematic, the population of human rotaviruses is genetically diverse, comprised of multiple genogroups that are further made up of numerous distinct genotypes. Genogroup II (GII) noroviruses are responsible for about 70% of human illness, while Genogroup I (GI) noroviruses are responsible for about 10%. Because norovirus antigenicity can rapidly evolve by mutation and recombination, norovirus vaccines will probably have to be updated regularly to reflect the antigenicity of contemporary circulating virus strains. The norovirus genome contains three large open reading frames (ORF1-ORF3). ORF2 encodes the 60-kDa major capsid protein VP1. Structurally, the VP1 protein resolves into two domains: shell(S) and protruding (P) (FIG. 8). The P domain is resolved into P1 and P2 subdomains, with the P1 subdomain forming the intervening stalk positioned between the S domain and the outermost P2 subdomain. P2 contains epitopes for neutralizing/blocking antibodies and mediates norovirus interactions with host cell glycans, including histo-blood group antigens. Expression of the norovirus capsid protein (VP1) alone leads to the self-assembly of virus-like particles (VLPs) that can induce immunological protective responses, including the production of anti-norovirus (IgA) antibodies (3). In this disclosure, recombinant SA11 rotaviruses have been generated wherein through the activity of a 2A self-cleavage element inserted into the segNSP3 dsRNA, the recombinant SA11 rotaviruses are expected to produce norovirus P2 as a separate protein.

Recombinant SA11 viruses expressing norovirus P2 and/ or P. Building on the positive results obtained with SA11 viruses containing a segNSP3-R2A/FL/UnaG genome segment, its NSP3-FUnaG ORF was redesigned, replacing the UnaG portion with the P2 and/or P ORF of norovirus (GII.4) MDA145. These recombinant virus have recently been recovered and confirmed by sequencing that it contains the expected segNSP3 dsRNA. The virus grows as efficiently as wildtype virus, indicating that the P2 and/or P products are not toxic. This is the first report of the recovery of a recombinant rotavirus carrying norovirus genetic material.

Expression of different manifestations of the P (domain) protein drives the formation of P-protein complexes, including the P dimer and P particle; there is evidence that these complexes can also induce protective responses in immunized animals. The effectiveness of VLPs and P-complexes as vaccines may depend on their ability to stimulate secretory gut IgA responses, a factor that may be influenced by co-administered adjuvants. In the case of an oral rotavirus-norovirus combination vaccine, rotavirus replication itself may provide an adjuvant like function that drives a more robust MHC presentation of the norovirus capsid protein in gut-associated lymphoid tissue, leading to a stronger and longer-lived mucosal antibody response. The ability of an oral rotavirus-norovirus combination vaccine to induce protective responses against rotaviruses and noroviruses can be evaluated using the gnotobiotic piglet model system. In past experiments performed with virulent and (vaccine-surrogate) attenuated strains of human G1P [8] Wa rotavirus, the piglet system has provided important insight into the nature of protective responses induced by oral vaccination. The piglet model system has also been developed as a tool to study the effectiveness of the norovirus P protein in inducing protective responses against virulent human noroviruses.

Norovirus vaccines currently under development are generally formulated from adjuvant-supplemented norovirus VLPs or P complexes. The combined rotavirus-norovirus vaccine can be targeted for use in young children and would replace currently used rotavirus vaccines. As such, the rotavirus-norovirus vaccine would not require the introduction of a separate norovirus immunization regiment into childhood immunization schedules. Moreover, the cost of developing and administering a combined rotavirus-norovirus vaccine could be considerably less than developing and administering two separate vaccines-one for rotavirus and the other for norovirus. Finally, on a global scale, the development of a live-oral vaccine rotavirus-based norovirus vaccine would enable the current rotavirus vaccine pipeline into the developing world to be used as a conduit to reach infants and young children without the need to develop an independent vaccination strategy against norovirus.

Figure 12:
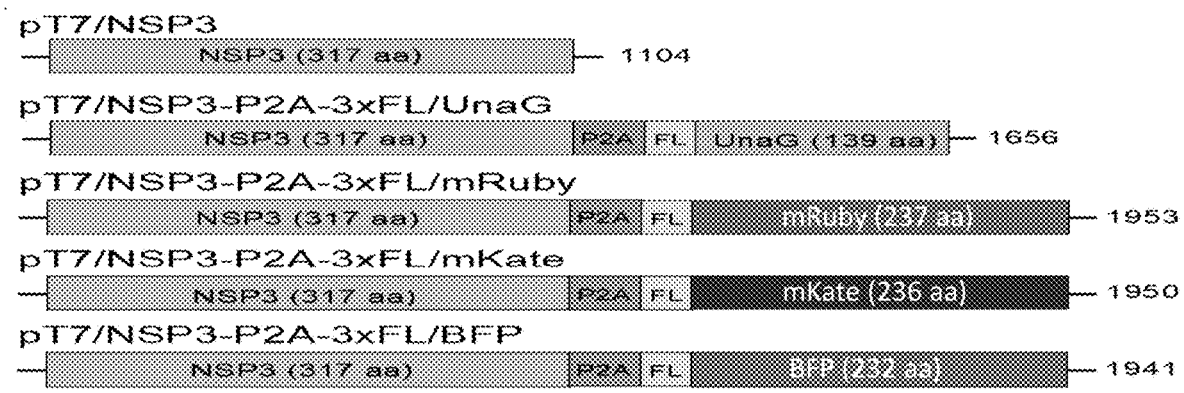
Figure 13:
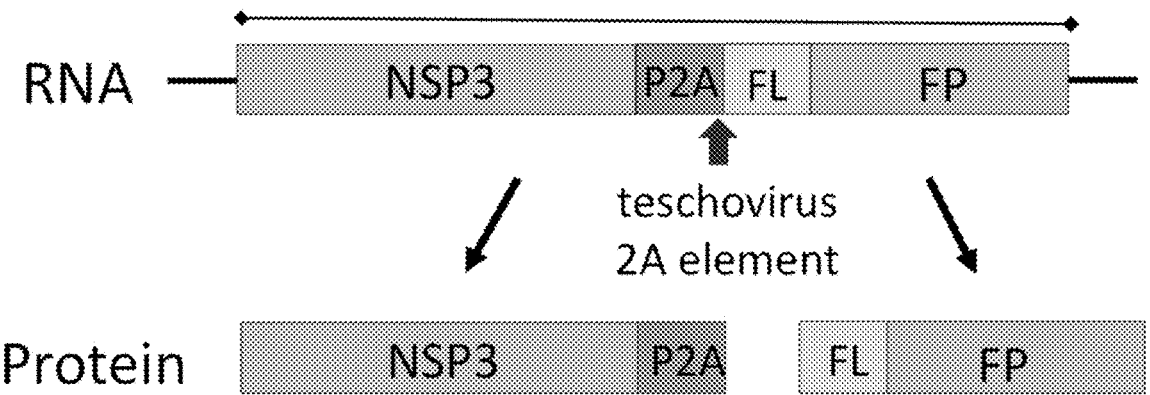
Figure 14:
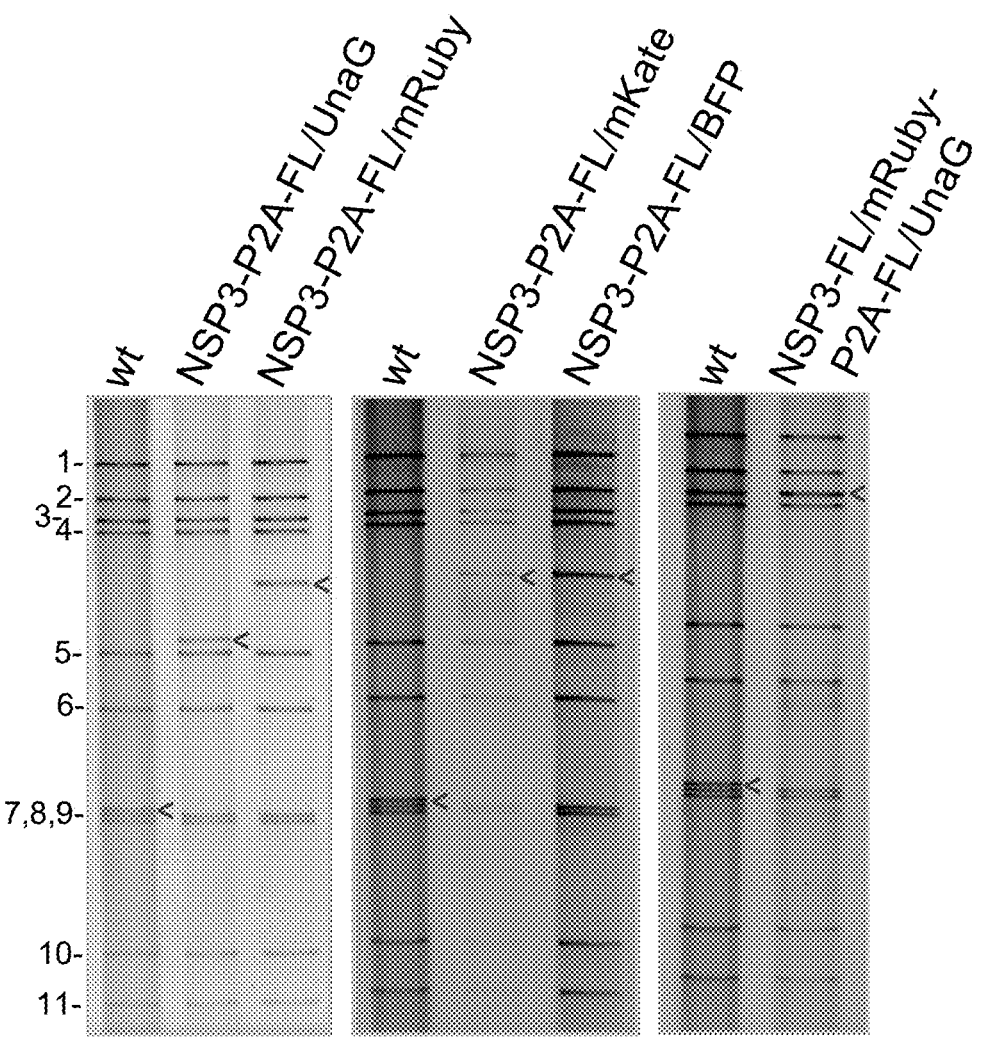
Figure 15:
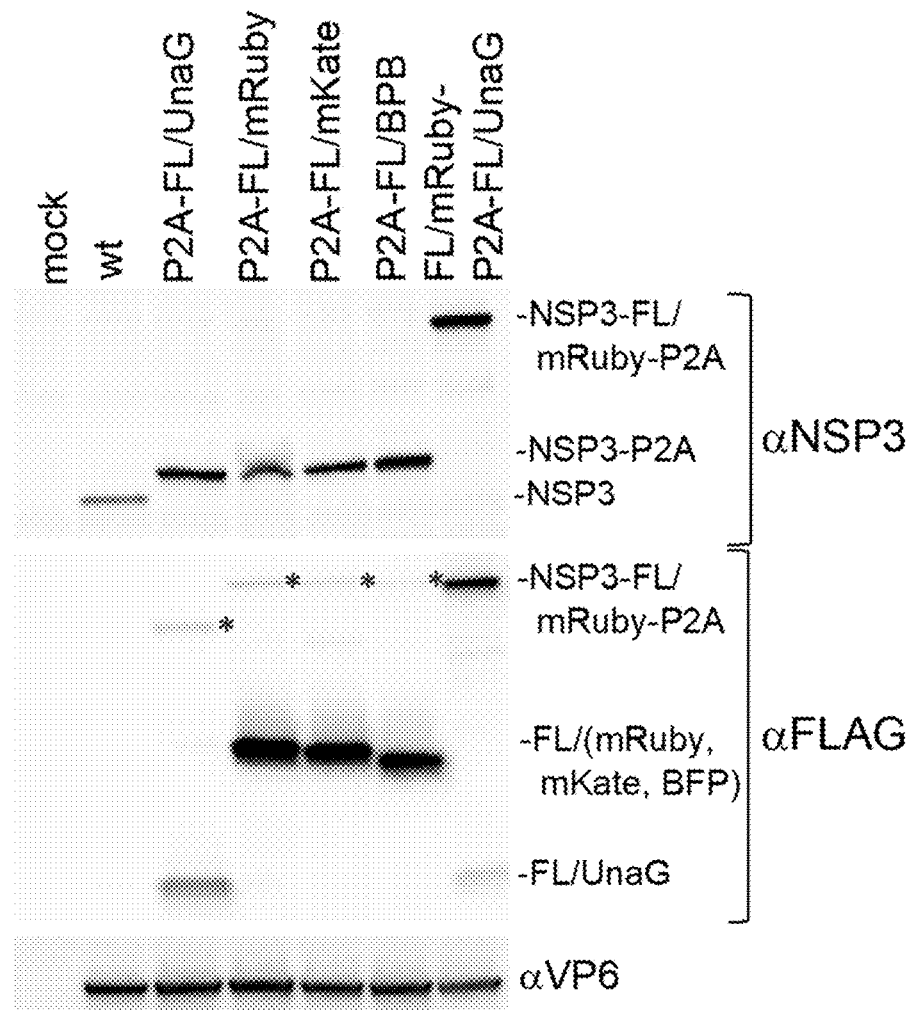
Figure 16:
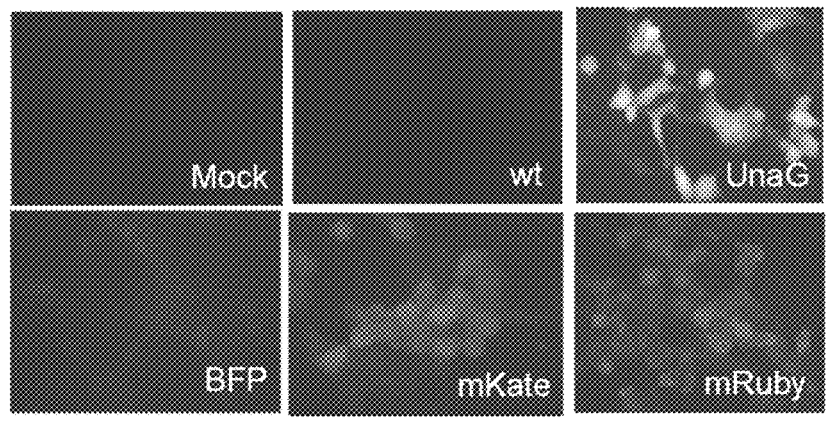

Expression of fluorescent proteins using a 2A translation element. Following the success of expressing UnaG (139aa) from the recombinant rotavirus expression system, it was explored whether other, larger fluorescent proteins could be expressed from the same system. As with UnaG, rotavirus gene 7 pT7 plasmids were modified to produce one of mRuby (237aa), mKate (236 aa) or BFP (232aa). Plasmid design is depicted in FIG. 12, which illustrates a 2A element downstream of the NSP3 ORF, followed by the ORF of a Flag-tagged fluorescent protein. This arrangement produced two proteins from the modified gene 7 ORF-NSP3 and the fluorescent protein (see FIG. 13). FIG. 14 represents the dsRNA genomes of the resulting recombinant viruses (RNA PAGE). Gene 7 dsRNA is indicated by the arrows. FIGS. 15 (PAGE/Western blot) and 16 (live-cell imaging) demonstrate successful expression of the various fluorescent proteins.

Figure 17:
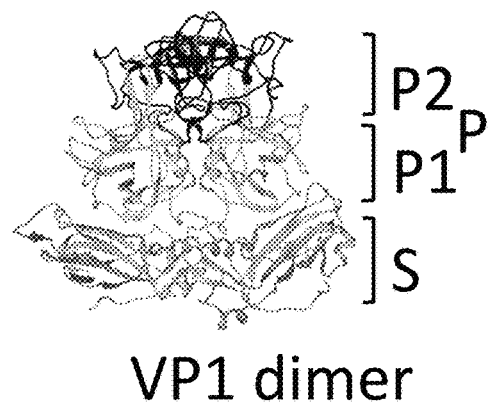
Figure 17:
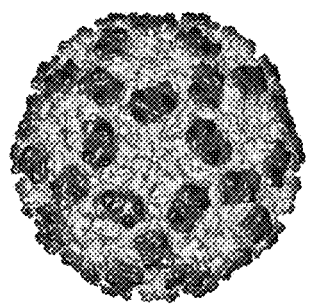
Figure 18:
Figure 18:
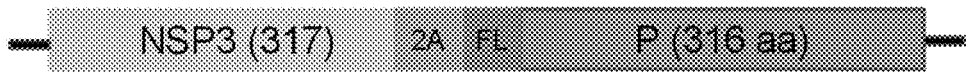
Figure 18:
Figure 19:
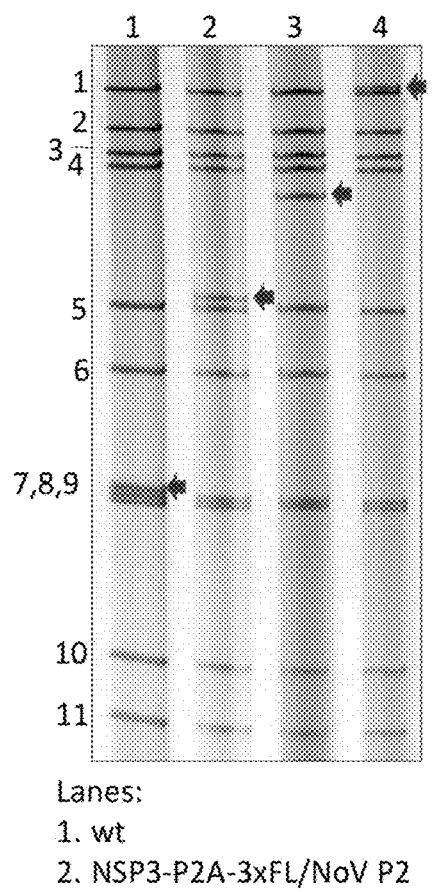
Figure 20:
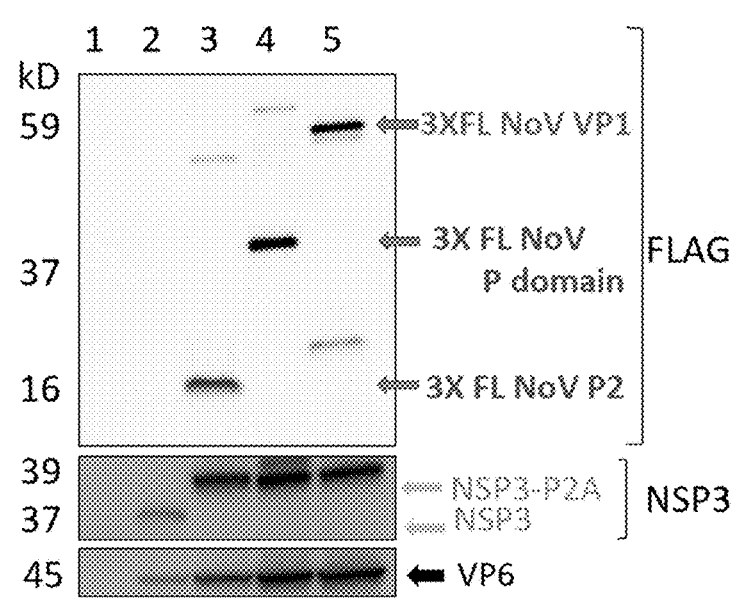

Expression of human norovirus capsid proteins from recombinant rotavirus expression systems. The norovirus capsid protein VP1 is a dimer that includes an S domain and a P domain, the P domain itself having P1 and P2 subdomains. See FIG. 17. Rotavirus gene 7 pT7 plasmids were modified to encode either the P2 subdomain (144aa), the full P domain (316aa), or full-length VP1 (540aa). FIG. 18 illustrates the plasmid design, where a 2A element was placed downstream of the NSP3 ORF, followed by the ORF of Flag-tagged norovirus capsid protein. FIG. 19 represents the dsRNA genomes of the resulting recombinant viruses (RNA PAGE). Gene 7 dsRNA is indicated by the arrows. Protein products expressed from the modified gene 7 pT7 plasmid were examined by PAGE/Western blot (FIG. 20). Each of P2, P, and VP1 were successfully expressed using the recombinant rotavirus expression system.

These results confirm that rotavirus can be modified to express norovirus capsid protein. The resulting recombinant rotavirus can be used in a combined rotavirus-norovirus vaccine.

Expression of human Astrovirus capsid proteins from recombinant rotavirus express systems. The human Astrovirus (HAstrV) capsid protein VP90 includes an acidic domain and VP70, which itself includes a shell domain, and P1 and P2 domains. See FIG. 21. Rotavirus gene 7 pT7 plasmids were modified to encode either the HAstrV P2 subunit (233 aa) or the full-length VP90 (818aa). FIG. 22 illustrates the plasmid design where a 2A element was placed downstream of the NSP3 ORF, followed by the ORF of Flag-tagged HAstrV capsid protein. FIGS. 19 (P2) and 20 (VP90) represent the dsRNA genomes of the resulting recombinant viruses (RNA PAGE). Gene 7 dsRNA is indicated by the arrows.

These results indicate that rotavirus can be used as an effective plug-and-play expression vector that can be used to direct expression of foreign proteins. Fusion of 2A-ORF cassettes to gene segment 7 NSP3 ORF can be used to generate rotaviruses that express foreign proteins in addition to the 12 viral proteins, and the expressed foreign proteins are genetically stable. Further, the recombinant rotaviruses can be produced that are capable of carrying >15% extra genetic material (>2.5 KB), allowing for the expression of a foreign protein having a size of about 90 kD.

Construction of G1P [8]-based expression system. 10 of the necessary pT7 G1P [8] vectors have been successfully constructed to date, and no problems are anticipated in preparing the last vector. These vectors have been combined with vectors of SA11 to produce reassortant, recombinant viruses, indicating that the G1P [8] vectors are functional. These data demonstrate the ability to base a recombinant rotavirus expression system on rotavirus strain G1P [8].

Development of recombinant rotavirus as vectors against other diseases. Capsid proteins of many other enteric and mucosal viruses could be introduced into rotavirus in a manner analogous to the approach used for the norovirus capsid protein. This could include hepatitis A virus (HAV), hepatitis C virus (HCV), hepatitis E virus (HEV), poliovirus, and astroviruses. This could also include not only viruses causing disease in human, but also diseases in livestock (cattle, swine, equine, poultry) and other animals. Similarly, cloning of bacterial genes into the rotavirus genome could lead to the recombinant viruses capable of inducing protective immune responses against bacteria in vaccines.

TABLE 1

Exemplary List of Enteric Viruses

| Enteric Viruses | Foreign Protein* |
|---|---|
| Enteroviruses | |
| Poliovirus | VP1 subunit, capsid protein |
| Coxsackie virus | VP1 subunit, capsid protein |
| Enteroviruses (types 68-71) | VP1 subunit, capsid protein |
| Hepatitis A Virus | VP2/VP3 subunit, capsid protein |
| Hepatitis C Virus | E1-glyprotein protruding domain |
| Hepatitis E Virus | Protruding (P) domain, capsid protein |
| Caliciviruses | Protruding (P) domain, capsid protein |
| Astroviruses | Outer capsid spike (P2) domain |
| Parechovirus | VP0 subunit, capsid protein |
| Reovirus | Head domain, S1 capsid protein |
| Adenovirus | Penton, capsid protein |
| Toroviruses | Spike glycoprotein, capsid |
| Picornavirus | VP1 subunit, capsid protein |
| Coronavirus | Spike glycoprotein, capsid |

*Proteins that can be expressed as separate proteins by recombinant rotaviruses, potentially yielding dual vaccines inducing immunological protective responses against rotavirus and other enteric viruses.

Development of recombinant rotaviruses originating from other host animal species. SA11 rotaviruses are a simian strain, and may not be ideally suited for generating human vaccine candidate virus strains. By replacing the pT7SA11 plasmids with equivalent plasmids containing rotavirus sequences instead from humans, porcine, bovine, equine, chicken, turkey, etc, strains of rotavirus, vaccine virus strains can be generated that are better suited to cause appropriate protective immune responses in other host species.

Materials and Methods

Cells

BHK-T7 cells: Gift from Dr. Ula Buchholz, Lab of Infectious Diseases, NIAID, NIH, Bethesda, MD; MA104 cells: ATTC [https://www.atcc.org/Products/All/CRL-2378.1.aspx]

Plasmids

SA11 pT7 plasmids: The complete set of plasmids used by Kanai et al (2017) to generate rRV (recombinant rotavirus) by reverse genetics were provided by Takeshi Kobyashi through the Addgene plasmid repository [https://www.addgene.org/browse/article/25158/].

pCMV-NP868R: Plasmid was generated in the Patton laboratory. To generate the pCMV-NP868R plasmid, a DNA representing the ASFV NP868R ORF (Genbank NP_042794), bounded by upstream XbaI and downstream BamHI sites, was commercially synthesized by Genscript and inserted into the EcoRV site of the pUC57 plasmid. A DNA fragment containing the NP868R ORF was recovered from the plasmid by digestion with NotI and PvuI and ligated into the plasmid pCMV-Script (Agilent Technologies), cut with the same two restriction enzymes. The Genbank accession numbers pCMV-NP868R (MH212166).

mGood plasmid: Plasmid was a gift from Dr. Maya Shmulevitz, University of Alberta. Plasmid contained an insert that included porcine teschovirus 2A element-3× Flag tag-UnaG (P2A-3xFL/UnaG).

Norovirus (NoV VP1) MD145 plasmid. A cDNA of the VP1 gene of human norovirus (NoV) strain (MD145) was commercially synthesized by Genewiz and inserted into a carrier plasmid. The VP1 protein forms the NoV capsid and consists of two major domains: protruding (P) and shell(S). The domain resolves into two additional domains: P1 and P2. The P2 domain contains antigenic epitopes that are likely recognized by host antibodies, leading to virus inactivation.

pT7-NSP3SA11/P2A-3×FL-UnaG: Plasmid was produced in the Patton lab by genetic manipulation of the Addgene plasmid pT7-NSP3SA11 [https://www.addgene.org/browse/article/25158/]. The mGood plasmid was used a template in PCR amplification reactions designed to generate a fragment containing the P2A-3×FL/UnaG sequence. The fragment was inserted into the pT7NSP3SA11 immediately downstream of the last coding codon of the NSP3 ORF, producing the plasmid pT7-NSP3SA11/P2A-3×FL-UnaG.

pT7-NSP3SA11/P2A-3×FL-NOV/P2. Plasmid was produced in the Patton lab by genetic manipulation of the Addgene plasmid pT7-NSP3SA11 [https://www.addgene.org/browse/article/25158/]. The Norovirus (NoV VP1) MD145 plasmid was used in PCR amplification reactions designed to generate a fragment corresponding to the P2 domain of the norovirus capsid protein. Standard cloning techniques were used to replace the UnaG sequence in the pT7-NSP3SA11/P2A-3×FL-UnaG plasmid with the P2 sequence.

pT7-NSP3SA11/P2A-3×FL-Nov/P. Plasmid was produced in the Patton lab by genetic manipulation of the Addgene plasmid pT7-NSP3SA11 [https://www.addgene.org/browse/article/25158/]. The Norovirus (NoV VP1) MD145 plasmid was used in PCR amplification reactions designed to generate a fragment corresponding to the P domain of the norovirus capsid protein. Standard cloning techniques were used to replace the UnaG sequence in the pT7-NSP3SA11/P2A-3×FL-UnaG plasmid with the P sequence.

rSA11g7/P2A-3×FL-UnaG: SA11 rRV that encodes the 12 full-length protein of wildtype SA11 virus, plus an extra protein (UnaG) through 2A activity. The rRV was generated using the modified NP868R-based RG system and the pT7-NSP3SA11/P2A-3×FL-UnaG plasmid. Virus was plaque purified and analyzed by gel electrophoresis, Western blot assay, and fluorescence microscopy.

rSA11g7/P2A-3×FL-NOV/P2: SA11 rRV that encodes the 12 full-length protein of wildtype SA11 virus, plus an extra protein (NoV/P2) through 2A activity. The rRV was generated using the modified NP868R-based RG system and the pT7-NSP3SA11/P2A-3×FL-Nov/P2 plasmid. Virus was plaque purified and analyzed by gel electrophoresis, Western blot assay, and fluorescence microscopy.

rSA11g7/P2A-3×FL-Nov/P: SA11 rRV that encodes the 12 full-length protein of wildtype SA11 virus, plus an extra protein (NoV/P) through 2A activity. The rRV was generated using the modified NP868R-based RG system and the pT7-NSP3SA11/P2A-3×FL-Nov/P plasmid. Virus was plaque purified and analyzed by gel electrophoresis, Western blot assay, and fluorescence microscopy.

Method for generating recombinant viruses. A modification of the plasmid-based reverse genetics system reported by Kanai et al (2017) was used to generate rRVs. Day 0: BHK-T7 cells were seeded into 12-well plates (about $2\times10^5$ cells/well) in G418-free Glasgow/FBS+medium. Day 1: Plasmid mixture was prepared that contained 0.8 µg each of the 11 SA11 rotavirus pT7 plasmids and 0.8 µg of pCMV-NP868R. The plasmid combination was added to 100 µl of pre-warmed (37° C.) Opti-MEM (Gibco, 31985-070) and mixed by gently pipetting up and down. Afterwards, 25 µl of TransIT-LTI transfection reagent (Mirus, MIR2305) was added, and the transfection mixture gently vortexed and incubated at room temperature for 20 min. During the incubation period, BHK-T7 cells in 12-well plates were washed once with Glasgow/FBS-complete medium and the cells overlaid with 1 ml of SMEM complete medium [MEM Eagle Joklik (Lonza 04-719Q), 10% tryptone-peptide broth, 2% NEAA, 1% penicillin-streptomycin, 1% glutamine). The transfection mixture was added drop-by-drop to the SMEM complete medium in the 12-well plates and the plates returned to a 37° C., 5% CO2 incubator. Day 3:2 ×105 MA104 cells in 0.25 ml of M199/FBS-free complete medium were added to plate wells, along with trypsin to a final concentration of 0.5 µg/ml. Day 6: Cells in plates were freeze-thawed 3-times and the lysates were placed in 1.5 ml microfuge tubes. After centrifugation at 500×g for 10 min (4° C.), 300 µl of the clarified lysates were transferred onto MA104 monolayers in 6-well plates containing 2 ml of M199/FBS-free complete medium and 0.5 g/ml trypsin. The plates were incubated in a 37°° C., 5% CO2 incubator for 7 days or until complete cytopathic effects (CPE) were observed. Typically, complete CPE occurred at 4-6 days for wells containing rRV. Recombinant viruses are plaque purified and analyzed by sequencing.

While the disclosed subject matter is amenable to various modifications and alternative forms, specific embodiments are described herein in detail. The intention, however, is not to limit the disclosure to the particular embodiments described. On the contrary, the disclosure is intended to cover all modifications, equivalents, and alternatives falling within the scope of the disclosure as defined by the appended claims.

Similarly, although illustrative methods may be described herein, the description of the methods should not be interpreted as implying any requirement of, or particular order among or between, the various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As the terms are used herein with respect to ranges, "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

What is claimed is:

1. A recombinant rotavirus comprising a gene segment including a nucleotide sequence encoding an intact, full-length rotavirus nonstructural protein 3 (NSP3) and a nucleotide sequence encoding a non-rotavirus polypeptide, wherein the NSP3 and the non-rotavirus polypeptide are encoded by a single open reading frame, separated by a self-cleavage protease domain.

2. The recombinant rotavirus of claim 1, wherein the self-cleavage protease domain is a 2A cleavage element.

3. The recombinant rotavirus of claim 1, wherein the non-rotavirus polypeptide is derived from a virus selected from the group consisting of: norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

4. The recombinant rotavirus of claim 1, wherein the non-rotavirus polypeptide induces an immunological response against a second virus that is not rotavirus.

5. The recombinant rotavirus of claim 1, wherein the non-rotavirus polypeptide induces an immunological response against a virus selected from the group consisting of: norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

6. The recombinant rotavirus of claim 1, wherein the non-rotavirus polypeptide is selected from the group consisting of norovirus VP1 protein, norovirus P domain, and norovirus P2 domain.

7. The recombinant rotavirus of claim 1, wherein the recombinant rotavirus is based upon serotype G1P [8].

8. An immunogenic composition comprising the recombinant rotavirus of claim 1.

9. The immunogenic composition of claim 8, wherein the immunogenic composition is formulated for oral, subcutaneous, or intramuscular administration.

10. A recombinant rotavirus expression system comprising:
   a nonstructural protein 3 (NSP3) expression vector including a nucleotide sequence encoding an intact, full-length rotavirus (NSP3) and a nucleotide sequence encoding a non-rotavirus polypeptide, wherein the NSP3 and the non-rotavirus polypeptide are encoded by a single open reading frame, separated by a self-cleavage protease domain;
   a VP1 expression vector;
   VP2 expression vector;
   a VP3 expression vector;
   a VP4 expression vector;
   a VP6 expression vector;
   a VP7 expression vector;
   a NSP1 expression vector;
   a NSP2 expression vector;
   a NSP4 expression vector;
   a NSP5/6 expression vector; and
   an African Swine Fever Virus NP868R RNA capping enzyme expression vector.

11. The recombinant rotavirus expression system of claim 10, wherein each of the NSP3 expression vector, VP1 expression vector, VP2 expression vector, VP3 expression vector, VP4 expression vector, VP6 expression vector, VP7 expression vector, NSP1 expression vector, NSP2 expression vector, NSP4 expression vector, and NSP5/6 expression vector are T7 expression vectors.

12. The recombinant rotavirus expression system of claim 10, wherein the self-cleavage protease domain is a 2A cleavage element.

13. The recombinant rotavirus expression system of claim 10, wherein the non-rotavirus polypeptide is derived from a virus selected from the group consisting of: norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

14. The recombinant rotavirus expression system of claim 10, wherein the non-rotavirus polypeptide induces an immunological response against a virus selected from the group consisting of: norovirus, enterovirus, poliovirus, coxsackie virus, hepatitis A virus, hepatitis C virus, hepatitis E virus, calicivirus, astrovirus, parechovirus, reovirus, adenovirus, torovirus, picornavirus, and coronavirus.

15. The recombinant rotavirus expression system of claim 10, wherein the non-rotavirus polypeptide is selected from the group consisting of norovirus VP1 protein, norovirus P domain, and norovirus P2 domain.

16. The recombinant rotavirus expression system of claim 10,
wherein the rotavirus reverse genetics system is based upon serotype G1P [8].

17. A method for producing a recombinant rotavirus, the method comprising:
transfecting BHK-T7 cells with the recombinant rotavirus expression system of claim 10;
overseeding the transfected BHK-T7 cells with MA104 cells;
preparing a clarified cell lysate; and
isolating recombinant rotavirus.

\* \* \* \* \*